United States Patent
Oguro et al.

(10) Patent No.: US 11,952,344 B2
(45) Date of Patent: Apr. 9, 2024

(54) HETEROCYCLIC COMPOUND AND USE THEREOF

(71) Applicant: TAKEDA PHARMACEUTICAL COMPANY LIMITED, Osaka (JP)

(72) Inventors: Yuya Oguro, Fujisawa (JP); Makoto Kamata, Fujisawa (JP); Shuhei Ikeda, Fujisawa (JP); Takeshi Wakabayashi, Fujisawa (JP); Norihito Tokunaga, Fujisawa (JP); Taku Kamei, Fujisawa (JP); Mitsuhiro Ito, Fujisawa (JP); Shigemitsu Matsumoto, Fujisawa (JP); Hirotaka Kamitani, Fujisawa (JP); Takaharu Hirayama, Fujisawa (JP); Toshio Tanaka, Fujisawa (JP); Hiroshi Banno, Fujisawa (JP); Nobuyuki Takakura, Fujisawa (JP); Jinichi Yonemori, Fujisawa (JP); Takuya Fujimoto, Fujisawa (JP)

(73) Assignee: Takeda Pharmaceutical Company Limited, Osaka (JP)

(*) Notice: Subject to any disclaimer, the term of this patent is extended or adjusted under 35 U.S.C. 154(b) by 42 days.

(21) Appl. No.: 17/754,118

(22) PCT Filed: Sep. 25, 2020

(86) PCT No.: PCT/IB2020/000772
§ 371 (c)(1),
(2) Date: Mar. 24, 2022

(87) PCT Pub. No.: WO2021/059017
PCT Pub. Date: Apr. 1, 2021

(65) Prior Publication Data
US 2022/0340527 A1    Oct. 27, 2022

(30) Foreign Application Priority Data
Sep. 25, 2019   (JP) .................... 2019-174311

(51) Int. Cl.
| | | |
|---|---|---|
| C07D 213/61 | (2006.01) | |
| A61K 31/444 | (2006.01) | |
| A61K 31/495 | (2006.01) | |
| A61P 25/00 | (2006.01) | |
| A61P 29/00 | (2006.01) | |
| C07D 211/04 | (2006.01) | |
| C07D 213/65 | (2006.01) | |
| C07D 213/68 | (2006.01) | |
| C07D 221/04 | (2006.01) | |
| C07D 237/08 | (2006.01) | |
| C07D 239/26 | (2006.01) | |
| C07D 239/34 | (2006.01) | |
| C07D 333/38 | (2006.01) | |
| C07D 401/12 | (2006.01) | |
| C07D 405/02 | (2006.01) | |

(52) U.S. Cl.
CPC .......... *C07D 211/04* (2013.01); *C07D 237/08* (2013.01); *C07D 239/26* (2013.01); *C07D 405/02* (2013.01)

(58) Field of Classification Search
CPC ............... C07D 213/61; C07D 213/65; C07D 213/68; C07D 221/04; C07D 239/34; C07D 333/38; C07D 401/12; A61K 31/495; A61K 31/444; A61P 25/00; A61P 29/00
See application file for complete search history.

(56) References Cited

U.S. PATENT DOCUMENTS

| | | |
|---|---|---|
| 4,382,938 A | 5/1983 | Kaplan et al. |
| 5,252,563 A | 10/1993 | Cordi et al. |
| 5,672,469 A | 9/1997 | Hioki et al. |
| 5,840,732 A | 11/1998 | Takatani et al. |
| 6,331,640 B1 | 12/2001 | Fotouhi et al. |
| 6,387,938 B1 | 5/2002 | Mizuguchi et al. |
| 6,420,415 B1 | 7/2002 | Yamashita et al. |
| 9,469,601 B2 | 10/2016 | Vacher et al. |

(Continued)

FOREIGN PATENT DOCUMENTS

| | | |
|---|---|---|
| AU | 2019204448 B2 | 7/2019 |
| AU | 2021225156 B2 | 9/2021 |

(Continued)

OTHER PUBLICATIONS

Davies, David J. et al., "A Novel Series of Benzimidazole NR2B-selective NMDA receptor antagonists", Biorganic & Medicinal Chemistry Letters, Elsevier, vol. 22, No. 7, Jan. 27, 2012 pp. 2620-2623.
International Search Report for International Application No. PCT/IB2020/000772, dated Jan. 22, 2021 (five pages).
Written Opinion for International Application No. PCT/US2020/000772 (nine pages), dated Jan. 22, 2021.

(Continued)

*Primary Examiner* — Bruck Kifle
(74) *Attorney, Agent, or Firm* — Finnegan, Henderson, Farabow, Garrett & Dunner LLP

(57) ABSTRACT

Provided is a heterocyclic compound that can have an antagonistic action on an NMD A receptor containing the NR2B subunit and that is expected to be useful as a prophylactic or therapeutic agent for depression, bipolar disorder, migraine, pain, peripheral symptoms of dementia and the like. A compound represented by the formula (I), wherein each symbol is as defined in the DESCRIPTION, or a salt thereof.

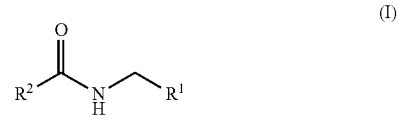

(I)

5 Claims, No Drawings

(56) References Cited

U.S. PATENT DOCUMENTS

| | | | |
|---|---|---|---|
| 10,202,376 | B2 | 2/2019 | Kimura et al. |
| 10,807,987 | B2 | 10/2020 | Oguro et al. |
| 11,230,541 | B2 | 1/2022 | Kimura et al. |
| 11,471,428 | B2 | 10/2022 | Hu et al. |
| 11,702,419 | B2 | 7/2023 | Oguro et al. |
| 11,713,311 | B2 | 8/2023 | Kimura et al. |
| 2002/0052512 | A1 | 5/2002 | Fotouhi et al. |
| 2003/0119811 | A1 | 6/2003 | Liverton et al. |
| 2004/0006236 | A1 | 1/2004 | Fotouhi et al. |
| 2004/0147568 | A1 | 7/2004 | Yu et al. |
| 2004/0204409 | A1 | 10/2004 | Ando et al. |
| 2005/0080119 | A1 | 4/2005 | Fotouhi et al. |
| 2005/0137187 | A1 | 6/2005 | Souers et al. |
| 2005/0165064 | A1 | 7/2005 | Kajino et al. |
| 2007/0155671 | A1 | 7/2007 | Fotouhi et al. |
| 2008/0234318 | A1 | 9/2008 | Gudmundsson et al. |
| 2009/0048303 | A1 | 2/2009 | Borza et al. |
| 2009/0099184 | A1 | 4/2009 | Delombaert et al. |
| 2010/0331335 | A1 | 12/2010 | Sham et al. |
| 2012/0238569 | A1 | 9/2012 | Gillespie et al. |
| 2012/0258950 | A1 | 10/2012 | Andrews et al. |
| 2013/0072494 | A1 | 3/2013 | Sham et al. |
| 2014/0315945 | A1 | 10/2014 | Campbell et al. |
| 2016/0031907 | A1 | 2/2016 | Campbell et al. |
| 2016/0244464 | A1 | 8/2016 | Campbell et al. |
| 2017/0362223 | A1 | 12/2017 | Kimura et al. |
| 2019/0300536 | A1 | 10/2019 | Oguro et al. |
| 2020/0231579 | A1 | 7/2020 | Kimura et al. |
| 2021/0332053 | A1 | 10/2021 | Oguro et al. |
| 2022/0089525 | A1 | 3/2022 | Oguro et al. |
| 2022/0388995 | A1 | 12/2022 | Kimura et al. |
| 2023/0002318 | A1 | 1/2023 | Ikeda et al. |
| 2023/0134307 | A1 | 5/2023 | Ikeda et al. |
| 2023/0150934 | A1 | 5/2023 | Ikeda et al. |

FOREIGN PATENT DOCUMENTS

| | | |
|---|---|---|
| EP | 1500658 A1 | 1/2005 |
| EP | 3 239 150 A1 | 11/2017 |
| EP | 3 342 772 A1 | 7/2018 |
| JP | 5798283 A | 6/1982 |
| JP | 8137043 A | 5/1996 |
| JP | 8319288 A | 12/1996 |
| JP | 2004161716 A | 6/2004 |
| JP | 2005511478 A | 4/2005 |
| JP | 2006-502162 A | 1/2006 |
| JP | 2006522794 A | 10/2006 |
| JP | 2008508248 A | 3/2008 |
| JP | 2009528992 A | 8/2009 |
| JP | 2012517439 A | 8/2012 |
| JP | 2013522171 A | 6/2013 |
| JP | 2014-510131 A | 4/2014 |
| JP | 2016502555 A | 1/2016 |
| WO | WO 98/01429 A1 | 1/1998 |
| WO | WO 00/21920 A1 | 4/2000 |
| WO | WO 01/30330 A2 | 5/2001 |
| WO | WO 01/32174 A1 | 5/2001 |
| WO | WO 02/072558 A1 | 9/2002 |
| WO | WO 02/080928 A1 | 10/2002 |
| WO | WO 03/035641 A1 | 5/2003 |
| WO | WO 2014/086825 A1 | 6/2004 |
| WO | WO 2007/027999 A2 | 3/2007 |
| WO | WO 2007/075387 A | 7/2007 |
| WO | WO 2007/078523 A2 | 7/2007 |
| WO | WO 2007/098352 A2 | 8/2007 |
| WO | WO 2009/004430 A1 | 1/2009 |
| WO | WO 2011/109441 A1 | 9/2011 |
| WO | WO 2012/123471 A1 | 9/2012 |
| WO | WO 2012/174199 A1 | 12/2012 |
| WO | WO 2014/134388 A1 | 9/2014 |
| WO | WO 2014/172044 A1 | 10/2014 |
| WO | WO 2015/127391 A1 | 8/2015 |
| WO | WO 2016/104434 A1 | 6/2016 |
| WO | WO 2017/027343 | 2/2017 |
| WO | WO 2017/027345 | 2/2017 |
| WO | WO 2017/174158 | 10/2017 |
| WO | WO 2019/022179 A1 | 1/2019 |
| WO | WO 2019/189945 | 10/2019 |
| WO | WO 2019/189945 A1 | 10/2019 |
| WO | WO 2020/081999 A1 | 4/2020 |
| WO | WO 2020/153414 A1 | 7/2020 |
| WO | WO 2020/154314 | 7/2020 |
| WO | WO 2020/196828 A1 | 10/2020 |
| WO | WO 2020/198710 A1 | 10/2020 |
| WO | WO 2021/094832 A1 | 5/2021 |

OTHER PUBLICATIONS

Borza et al., "Benzimidazole-2-carboxamides as novel NR2B selective NMDA receptor antagonists," Bioorganic & Medicinal Chemistry Letters, 2006, 16:4638-4640.

Caddy et al., "Ketamine as the prototype glutamatergic antidepressant: pharmacodynamic actions, and a systematic review and meta-analysis of efficacy," Ther. Adv. Psychopharmacol., 2014, 4:75-99.

Davies et al., "A novel series of benzimidazole NR2B-selective NMDA receptor antagonists," Bioorg. Med. Chem. Lett, 2012, 22:2620-2623.

Devonshire et al., "Effects of urethane anaesthesia on sensory processing in the rat barrel cortex revealed by combined optical imaging and electrophysiology," Eur. J. Neurosci., 2010, 32:786-797.

Extended European Search Report dated Oct. 19, 2020, for Corresponding European Patent Application 18838990.2 (11 pages).

Howlett et al., "Inhibition of fibril formation in b-amyloid peptide by a novel series of benzofurans," Biochem. J. 1999, 340 (1) :283-289.

Iadarola et al., "Ketamine and other N-methyl-D-aspartate receptor antagonists in the treatment of depression: a perspective review," Ther. Adv. Chronic. Dis. 2015, 6(3): 97-114.

Jin et al., "Developmental Expression, Subcellular Localization, and Tyrosine Phosphorylation of NR2A and NR2B in the Rat Brain," Mol. Cells, 1997, 7(1):64-71.

Kandiah et al., "Cerebral white matter disease is independently associated with BPSD in Alzheimer's disease," J. Neural. Sci. 2014, 337: 162-166.

Kim et al., "Effect of NMDA NR2B antagonist on neuropathic pain in two spinal cord injury models," Pain, 2012, 153: 1022-1029.

Maidment et al., "Efficacy of Memantine on Behavioral and Psychological Symptoms Related to Dementia: A Systematic Meta-Analysis," Ann. Pharmacother., 2008, 42: 32-38.

Monyer et al., "Developmental and Regional Expression in the Rat Brain and Functional Properties of Four NMDA Receptors," Neuron, 1994, 12:529-540.

Peeters et al., "Effects of Pan- and Subtype-Selective N-Methyl-D-aspartate Receptor Antagonists on Cortical Spreading Depression in the Rat: Therapeutic Potential for Migraine," J. Pharmacol. Exp. Ther. 2007, 321: 564-572.

Preskorn et al., "An Innovative Design to Establish Proof of Concept of the Antidepressant Effects of the NR2B Subunit Selective N-Methyl-D-Aspartate Antagonist, CP-101,606, in Patients With Treatment-Refractory Major Depressive Disorder," J. Clin. Psychopharmacol., 2008, 28:631-637.

Shityakov et al. "α-Cyclodextrin dimer complexes of dopamine and levodopa derivatives to assess drug delivery to the central nervous system: ADME and molecular docking studies," International Journal of Nanomedicine, 2012, 7:3211-3219.

Registry (STN) for CAS registration No. 1349423-75-1, 3-Pyridinecarboxamide, N-[2-chloro-4-cyanophenyl) methyl]-6-(3,3,3-trifluoropropoxy)-(CA Index Name) (entered Dec. 6, 2011) and CAS registration No. 1406153-87-4, Benzamide, N-[(4-cyano-2-fluorophenyl)methyl]-4-methoxy-(CA Index Name) (entered Nov. 25, 2012) (6 pages).

Thompson, et al. Document No. 170:112996, retrieved from STN, Dec. 13, 2018 (three pages).

Watanabe et al., "Distinct Distributions of Five N-Methyl-D-Aspartate Receptor Channel Subunit mRNAs in the Forebrain," The Journal of Comparative Neurology, 1993, 338:377-390.

(56) References Cited

OTHER PUBLICATIONS

Wu et al., "Targeting the NMDA Receptor Subunit NR2B for the Treatment of Neuropathic Pain," Neurotherapeutics, 2009, 6, 4:693-702.

Brown et al., "2,6-Disubstituted pyrazines and related analogs as NR2B site antagonists of the NMDA receptor with anti-depressant activity," Bioorganic & Medicinal Chemistry Letters, 2011, 21, 11:3399-3403.

Chemical Abstracts Service, Columbus, Ohio, US; Dec. 8, 2013, Aurora Fine Chemicals C: "-2-Thiophenecarboxamide, N-[(N-cyano-2-fluorophenyl) methyl]-4-methoxy-", XP055959594, Database accession No. 1510812-10-8, abstract (two pages).

Chemical Abstracts Service, Columbus, Ohio, US; Dec. 8, 2013, Aurora Fine Chemicals C: "-2- Thiophenecarboxamide, N-[(N-cyano-2-fluorophenyl) methyl]-4-methoxy-", XP055959595, Database accession No. 1489651-31-1, abstract (two pages).

Kawai et al., "Structure-activity relationship study of novel NR2B-selective antagonists with arylamides to avoid reactive metabolites formation", Bioorganic & Medicinal Chemistry Letters, 2007, 17, 5537-5542.

Taylor et al., "Design and Synthesis of Substituted Nicotinamides as Inhibitors of Soluble Epoxide Hydrolase," Bioorganic and Medicinal Chemistry Letters, 2009, 19: 5864-5868.

Jonas et al. "Differences in $Ca^{2+}$ permeability of AMPA-type glutamate receptor channels in neocortical neurons caused by differential GluR-B subunit expression," Neuron, 1994, 12: 1281-1289.

STN Registry Entry for "Benzeneacetamide, 2-chloro-N-(pyrazolo [1,5-a] pyrimidin-3-ylmethyl)" (1638470-82-2) (one page).

U.S. Appl. No. 17/010,666, filed Sep. 2, 2020 by Oguro et al.

HETEROCYCLIC COMPOUND AND USE THEREOF

This application is a national stage filing under 35 U.S.C. § 371 of International Application No. PCT/IB2020/000772, filed Sep. 25, 2020, which claims priority to JP 2019-174311, filed Sep. 25, 2019, the contents of each of which are incorporated by reference herein in their entirety.

TECHNICAL FIELD

The present invention relates to a heterocyclic compound that can have an antagonistic action on an N-methyl-D-aspartic acid (NMDA) receptor containing the NR2B subunit, and that is expected to be useful as a prophylactic or therapeutic agent for depression, bipolar disorder, migraine, pain, peripheral symptoms of dementia and the like.

BACKGROUND OF THE INVENTION

The major excitatory neurotransmitter in the central nervous system such as the brain, spinal cord and the like is glutamic acid, and its signal transduction is mediated by N-methyl-D-aspartic acid (NMDA) receptor, gamma-amino-3-hydroxy-5-methyloxazole-4-propionic acid (AMPA)/kainic acid (KA) receptor and metabotropic glutamate receptor. Of these, NMDA receptor is highly permeable to cations including calcium ion and mediate excitatory neurotransmission by depolarizing nerve cells. In addition, calcium flowing into the cell via NMDA receptor functions as a secondary messenger, and causes plastic changes in the nerve function through actions such as changes in the intracellular phosphorylation signal, regulation of transcription and translation of the gene, and the like. Thus, NMDA receptor plays an important role in the functional regulation of central nervous system.

The NMDA receptor is a receptor composed of a tetramer in which 2 to 3 subunits from among NR1, NR2A, NR2B, NR2C, NR2D, NR3A, NR3B subunits are associated, and, to have the function of a receptor responsible for excitatory neurotransmission, the presence of the NR1 subunit is essential. Since the NR1 subunit is contained in all NMDA receptors having the function, it is widely distributed in the central nervous system; however, the distribution and the timing of expression of the NR2 subunit are different for each subunit. For example, NR2A and NR2C subunits are detected only immediately before birth, whereas NR2B and NR2D subunits are observed from an early stage in embryonic development. For example, while the NR2A subunit is widely distributed in the brain, the NR2B subunit is locally expressed in the forebrain and the NR2C subunit is locally expressed in the cerebellum (non-patent document 1).

An NMDA receptor containing the NR2B subunit, which is the target in the present invention, is highly expressed in the cerebral cortex (particularly the second or third layer), hippocampus, amygdala, ventral nucleus of thalamus, and olfactory bulb in the brain of adult rodents. The NMDA receptor is confined to the dorsal horn of the spinal cord (particularly the second layer) in the spinal cord (non-patent document 2). Moreover, in a single cell, the NMDA receptor containing the NR2B subunit is most highly expressed in postsynaptic density and the expression is also found in the extrasynaptic region (non-patent document 3). This suggests that an NMDA receptor containing the NR2B subunit functions widely in the brain and is effective for the prophylaxis or treatment of central diseases.

Patent document 1 discloses the following compound having an antibacterial action and useful as a pesticide or the like:

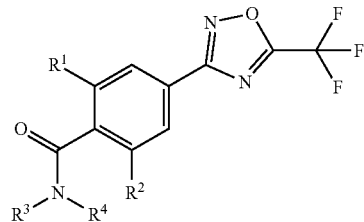

wherein each symbol is as defined in the document.

Patent document 2 discloses the following compound having a calcitonin gene-related peptide (CGPR) receptor antagonistic action and useful for the prophylaxis or treatment of migraine, nerve system disease and the like:

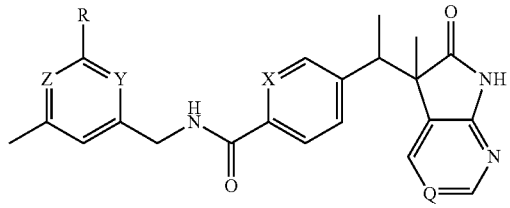

wherein each symbol is as defined in the document.

Patent document 3 discloses the following compound having a CGPR receptor antagonistic action and useful for the prophylaxis or treatment of migraine, nerve system disease and the like:

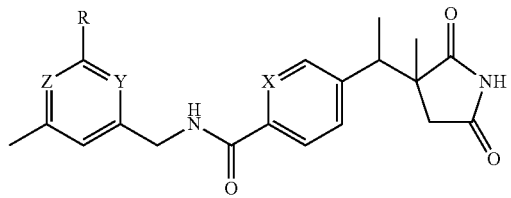

wherein each symbol is as defined in the document.

Patent document 4 discloses the following compound having a FXa inhibitory action and useful for antithrombosis, and the like:

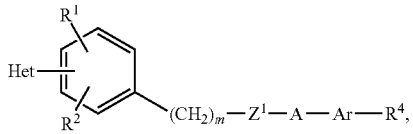

wherein each symbol is as defined in the document.

Patent document 5 discloses the following compound having an Enhancer of zeste homolog (EZH) inhibitory action and useful for the prophylaxis or treatment of cancer and the like:

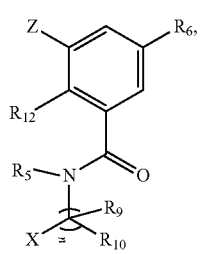

wherein each symbol is as defined in the document.

Patent document 6 discloses the following compound having an NMDA NR2B subunit specific negative allosteric modulator action and useful for the prophylaxis or treatment of major depression, bipolar disorder, migraine, pain, peripheral symptoms of dementia and the like:

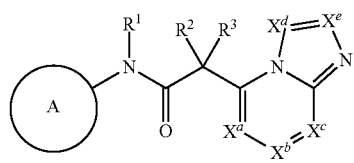

wherein each symbol is as defined in the document.

Patent document 7 discloses the following compound having an antagonistic action on N-methyl-D-aspartic acid (NMDA) receptors including NR2B subunit and useful for the prophylaxis or treatment of major depression, bipolar disorder, migraine, pain, peripheral symptoms of dementia and the like:

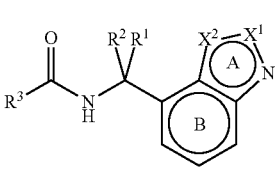

wherein each symbol is as defined in the document.

Patent document 8 discloses the following compound having an antagonistic action on N-methyl-D-aspartic acid (NMDA) receptor containing NR2B subunit and useful for the prophylaxis or treatment of major depression, bipolar disorder, migraine, pain, peripheral symptoms of dementia and the like:

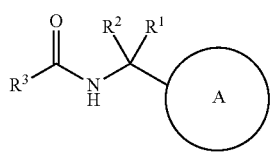

wherein each symbol is as defined in the document.

Patent document 9 discloses the following compound having an antagonistic action on N-methyl-D-aspartic acid (NMDA) receptor containing NR2B subunit and useful for the prophylaxis or treatment of major depression, bipolar disorder, migraine, pain, peripheral symptoms of dementia and the like:

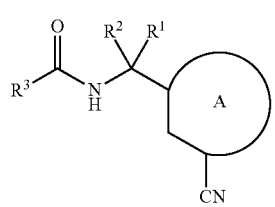

wherein each symbol is as defined in the document.

DOCUMENT LIST

Patent Documents

Patent document 1: WO 2017/174158
Patent document 2: WO 2017/027343
Patent document 3: WO 2017/027345
Patent document 4: WO 02/072558
Patent document 5: WO 2014/172044
Patent document 6: WO 2016/104434
Patent document 7: WO 2019/022179
Patent document 8: WO 2019/189945
Patent document 9: WO 2020/154314

Non-Patent Documents

Non-patent document 1: Neuron, vol. 12, pages 529-540, 1994
Non-patent document 2: The Journal of Comparative Neurology (J. Comp. Neurol.), vol. 338, pages 377-390, 1993
Non-patent document 3: Molecules and Cells (Mol. Cells), vol. 7, pages 64-71, 1997

SUMMARY OF INVENTION

Technical Problem

The present invention aims to provide a heterocyclic compound that can have an antagonistic action on NMDA receptor containing the NR2B subunit, and that is expected to be useful as a prophylactic or therapeutic agent for depression, bipolar disorder, migraine, pain, peripheral symptoms of dementia and the like, and a medicament containing the same.

Solution to Problem

The present inventors have conducted intensive studies in an attempt to solve the above-mentioned problems, and found that a compound represented by the following formula (I) can have a superior antagonistic action on an NMDA receptor containing the NR2B subunit, which resulted in the completion of the present invention.

That is, the present invention provides the following.

[1] A compound represented by the formula (I):

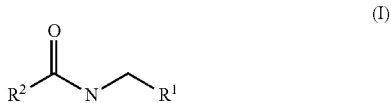

wherein
R¹ is

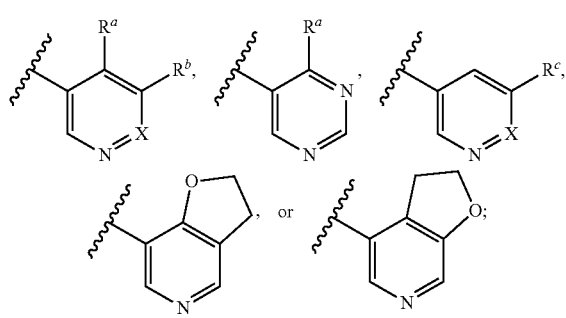

wherein
X is CH or a nitrogen atom;
R<sup>a</sup> is
(1) a C<sub>1-3</sub> alkyl group optionally substituted by fluorine atom(s),
(2) a C<sub>3-6</sub> cycloalkyl group optionally substituted by fluorine atom(s),
(3) a C<sub>1-6</sub> alkoxy group optionally substituted by fluorine atom(s), or
(4) a C<sub>3-6</sub> cycloalkyloxy group optionally substituted by fluorine atom(s);
R<sup>b</sup> is
(1) a hydrogen atom,
(2) a C<sub>1-6</sub> alkyl group optionally substituted by fluorine atom(s),
(3) a C<sub>1-6</sub> alkoxy group optionally substituted by fluorine atom(s), or
(4) a halogen atom; and
R<sup>c</sup> is
(1) a C<sub>2-6</sub> alkyl group optionally substituted by fluorine atom(s),
(2) a C<sub>1-6</sub> alkoxy group optionally substituted by fluorine atom(s), or
(3) a halogen atom; and
R² is
(1)

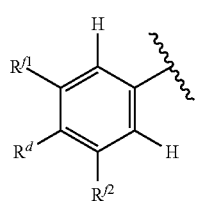

wherein
R<sup>d</sup> is
(a) a C<sub>3-6</sub> cycloalkyl group optionally substituted by fluorine atom(s),
(b) a C<sub>1-6</sub> alkoxy group optionally substituted by fluorine atom(s),
(c) a C<sub>3-6</sub> cycloalkyloxy group optionally substituted by fluorine atom(s),
(d) a difluoromethyl group, or
(e) a trifluoromethyl group; and
R<sup>f1</sup> and R<sup>f2</sup> are each independently a hydrogen atom, a fluorine atom, a chlorine atom, or a methyl group, (2)

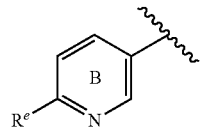

wherein
R<sup>e</sup> is
(a) a C<sub>3-6</sub> cycloalkyl group optionally substituted by fluorine atom(s),
(b) a C<sub>1-6</sub> alkoxy group optionally substituted by fluorine atom(s),
(c) a C<sub>3-6</sub> cycloalkyloxy group optionally substituted by fluorine atom(s), or
(d) a C<sub>1-2</sub> alkyl group substituted by fluorine atom(s); and
ring B is optionally further substituted by 1 to 3 substituents selected from a fluorine atom, a chlorine atom, and a methyl group, or
(3)

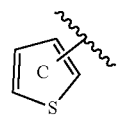

wherein
ring C is further substituted by 1 or 2 substituents selected from
(a) a C<sub>3-6</sub> cycloalkyl group optionally substituted by fluorine atom(s),
(b) a C<sub>1-6</sub> alkoxy group optionally substituted by fluorine atom(s),
(c) a C<sub>3-6</sub> cycloalkyloxy group optionally substituted by fluorine atom(s), and
(d) a C<sub>1-2</sub> alkyl group substituted by fluorine atom(s),
or a salt thereof (sometimes to be abbreviated as "compound (I)" in the present specification).

[2] The compound of [1], wherein R¹ is

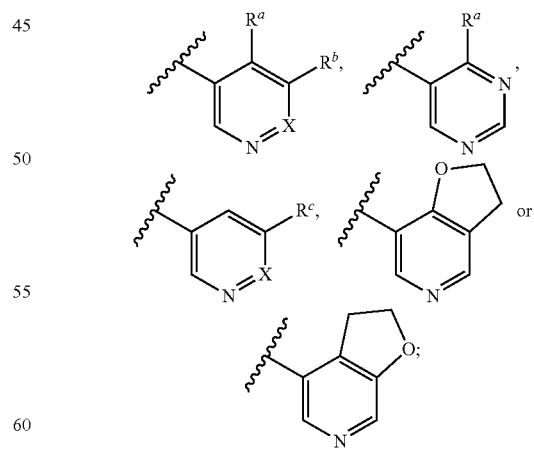

wherein
X is CH or a nitrogen atom;
R<sup>a</sup> is
(1) a C<sub>1-3</sub> alkyl group optionally substituted by 1 to 3 fluorine atoms, (2) a $C_{3-6}$ cycloalkyl group optionally substituted by 1 to 3 fluorine atoms,
(3) a $C_{1-6}$ alkoxy group optionally substituted by 1 to 3 fluorine atoms, or
(4) a $C_{3-6}$ cycloalkyloxy group optionally substituted by 1 to 3 fluorine atoms;
$R^b$ is
(1) a hydrogen atom, or
(2) a halogen atom; and
$R^c$ is
(1) a $C_{1-6}$ alkoxy group optionally substituted by 1 to 3 fluorine atoms, or
(2) a halogen atom; and
$R^2$ is
(1)

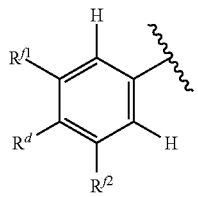

wherein
$R^d$ is
(a) a $C_{1-6}$ alkoxy group optionally substituted by 1 to 3 fluorine atoms,
(b) a difluoromethyl group, or
(c) a trifluoromethyl group; and
$R^{f1}$ and $R^{f2}$ are each independently a hydrogen atom, fluorine atom, or chlorine atom,
(2)

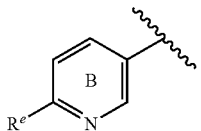

wherein
$R^e$ is
(a) a $C_{3-6}$ cycloalkyl group optionally substituted by 1 to 3 fluorine atoms,
(b) a $C_{1-6}$ alkoxy group optionally substituted by 1 to 3 fluorine atoms, or
(c) a $C_{1-2}$ alkyl group substituted by 1-5 fluorine atoms; and
ring B is optionally further substituted by 1 to 3 substituents selected from a fluorine atom, and a chlorine atom, or
(3)

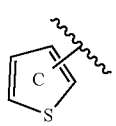

wherein
ring C is further substituted by 1 or 2 substituents selected from
(a) a $C_{3-6}$ cycloalkyl group optionally substituted by 1 to 3 fluorine atoms, and
(b) a $C_{1-2}$ alkyl group substituted by 1 to 3 fluorine atoms, or a salt thereof.

[3] A medicament comprising the compound of [1] or a salt thereof.

[4] The medicament of [3], wherein the medicament is an antagonist of an NMDA receptor containing an NR2B subunit.

[5] The medicament of [3], wherein the medicament is a prophylactic or therapeutic agent for depression, bipolar disorder, migraine, pain, or peripheral symptoms of dementia.

[6] The compound of [1] or a salt thereof for use in the prophylaxis or treatment of depression, bipolar disorder, migraine, pain, or peripheral symptoms of dementia.

[7] A method for antagonizing an NMDA receptor containing an NR2B subunit in a mammal, comprising administering an effective amount of the compound of [1] or a salt thereof to the mammal.

[8] A method for preventing or treating depression, bipolar disorder, migraine, pain, or peripheral symptoms of dementia in a mammal, comprising administering an effective amount of the compound of [1] or a salt thereof to the mammal.

[9] Use of the compound of [1] or a salt thereof for the production of a prophylactic or therapeutic agent for depression, bipolar disorder, migraine, pain, or peripheral symptoms of dementia.

Advantageous Effects of Invention

The present invention provides a heterocyclic compound that can have an antagonistic action on an NMDA receptor containing the NR2B subunit and that is expected to be useful as a prophylactic or therapeutic agent for depression, bipolar disorder, migraine, pain, peripheral symptoms of dementia and the like, and a medicament containing the same.

DETAILED DESCRIPTION OF THE INVENTION

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2- butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the optionally halogenated "$C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the optionally halogenated "$C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butyl sulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy), (8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, di methylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl)($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, di hydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and
9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ so alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl $C_{1-6}$ alkyl-carbonyl)amino group (e.g., N-acetyl-N-methylamino) and a ($C_{1-6}$ alkyl)($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a 06-14 arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

In the present specification, the "$C_{1-2}$ alkyl group" is, for example, the above-mentioned "$C_{1-6}$ alkyl group" having 1-2 carbon atoms, the "$C_{1-3}$ alkyl group" is, for example, the above-mentioned "$C_{1-6}$ alkyl group" having 1-3 carbon atoms, and the "$C_{2-6}$ alkyl group" is, for example, the above-mentioned "$C_{1-6}$ alkyl group" having 2-6 carbon atoms.

In the present specification, the "$C_{3-6}$ cycloalkyl group" is, for example, the above-mentioned "$C_{3-10}$ cycloalkyl group" having 3-6 carbon atoms.

In the present specification, the "$C_{3-6}$ cycloalkyloxy group" is, for example, the above-mentioned "$C_{3-10}$ cycloalkyloxy group" having 3-6 carbon atoms.

In the present specification, the "$C_{1-3}$ alkyl group optionally substituted by fluorine atom(s)" means, for example, the above-mentioned $C_{1-3}$ alkyl group optionally substituted by 1-5 (preferably 1-3) fluorine atoms, the "$C_{2-6}$ alkyl group optionally substituted by fluorine atom(s)" means, for example, the above-mentioned $C_{2-6}$ alkyl group optionally substituted by 1-5 (preferably 1-3) fluorine atoms, "a $C_{1-6}$ alkyl group optionally substituted by fluorine atom(s)" means, for example, the above-mentioned $C_{1-6}$ alkyl group optionally substituted by 1-5 (preferably 1-3) fluorine atoms.

In the present specification, the "$C_{3-6}$ cycloalkyl group optionally substituted by fluorine atom(s)" means, for example, the above-mentioned $C_{3-6}$ cycloalkyl group optionally substituted by 1-5 (preferably 1-3) fluorine atoms.

In the present specification, the "$C_{1-6}$ alkoxy group optionally substituted by fluorine atom(s)" means, for example, the above-mentioned $C_{1-6}$ alkoxy group optionally substituted by 1-5 (preferably 1-3) fluorine atoms.

In the present specification, the "$C_{3-6}$ cycloalkyloxy group optionally substituted by fluorine atom(s)" means, for example, the above-mentioned $C_{3-6}$ cycloalkyloxy group optionally substituted by 1-5 (preferably 1-3) fluorine atoms.

In the present specification, the "$C_{1-2}$ alkyl group substituted by fluorine atom(s)" means, for example, the above-mentioned $C_{1-2}$ alkyl group substituted by 1-5 (preferably 1-3) fluorine atoms.

The definition of each symbol in the formula (I) is explained below.

$R^1$ is

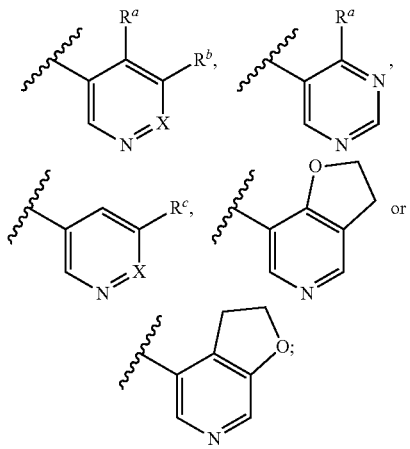

wherein

X is CH or a nitrogen atom;

$R^a$ is (1) a $C_{1-3}$ alkyl group optionally substituted by fluorine atom(s), (2) a $C_{3-6}$ cycloalkyl group optionally substituted by fluorine atom(s), (3) a $C_{1-6}$ alkoxy group optionally substituted by fluorine atom(s), or (4) a $C_{3-6}$ cycloalkyloxy group optionally substituted by fluorine atom(s);

$R^b$ is (1) a hydrogen atom, (2) a $C_{1-6}$ alkyl group optionally substituted by fluorine atom(s), (3) a $C_{1-6}$ alkoxy group optionally substituted by fluorine atom(s), or (4) a halogen atom; and $R^c$ is (1) a $C_{2-6}$ alkyl group optionally substituted by fluorine atom(s), (2) a $C_{1-6}$ alkoxy group optionally substituted by fluorine atom(s), or (3) a halogen atom.

X is preferably CH.

$R^a$ is preferably (1) a $C_{1-3}$ alkyl group (e.g., methyl, ethyl) optionally substituted by 1 to 3 fluorine atoms, (2) a C$_{3-6}$ cycloalkyl group (e.g., cyclopropyl, cyclobutyl) optionally substituted by 1 to 3 fluorine atoms,
(3) a C$_{1-6}$ alkoxy group (e.g., methoxy, ethoxy, isopropoxy) optionally substituted by 1 to 3 fluorine atoms, or
(4) a C$_{3-6}$ cycloalkyloxy group (e.g., cyclopropyloxy, cyclobutyloxy) optionally substituted by 1 to 3 fluorine atoms, more preferably,
(1) a C$_{1-3}$ alkyl group (e.g., methyl),
(2) a C$_{1-6}$ alkoxy group (e.g., methoxy, ethoxy), or
(3) a C$_{3-6}$ cycloalkyloxy group (e.g., cyclopropyloxy).

R$^b$ is preferably
(1) a hydrogen atom, or
(2) a halogen atom (e.g., fluorine atom, chlorine atom), more preferably,
(1) a hydrogen atom, or
(2) a fluorine atom.

R$^c$ is preferably
(1) a C$_{1-6}$ alkoxy group (e.g., methoxy) optionally substituted by 1 to 3 fluorine atoms, or
(2) a halogen atom (e.g., chlorine atom, bromine atom).

R$^1$ is preferably

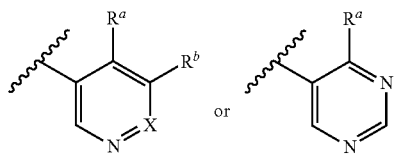

wherein each group is as defined above,
X is preferably CH;
R$^a$ is preferably
(1) a C$_{1-3}$ alkyl group (e.g., methyl),
(2) a C$_{1-6}$ alkoxy group (e.g., methoxy, ethoxy), or
(3) a C$_{3-6}$ cycloalkyloxy group (e.g., cyclopropyloxy); and R$^b$ is preferably
(1) a hydrogen atom, or
(2) a halogen atom (e.g., fluorine atom).

R$^2$ is
(1)

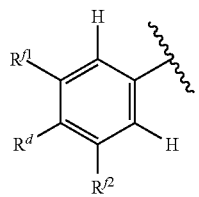

wherein
R$^d$ is
(a) a C$_{3-6}$ cycloalkyl group optionally substituted by fluorine atom(s),
(b) a C$_{1-6}$ alkoxy group optionally substituted by fluorine atom(s),
(c) a C$_{3-6}$ cycloalkyloxy group optionally substituted by fluorine atom(s),
(d) a difluoromethyl group, or
(e) a trifluoromethyl group; and
R$^{f1}$ and R$^{f2}$ are each independently a hydrogen atom, a fluorine atom, a chlorine atom, or a methyl group, (2)

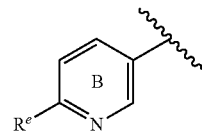

wherein
R$^e$ is
(a) a C$_{3-6}$ cycloalkyl group optionally substituted by fluorine atom(s),
(b) a C$_{1-6}$ alkoxy group optionally substituted by fluorine atom(s),
(c) a C$_{3-6}$ cycloalkyloxy group optionally substituted by fluorine atom(s), or
(d) a C$_{1-2}$ alkyl group substituted by fluorine atom(s); and
ring B is optionally further substituted by 1 to 3 substituents selected from a fluorine atom, a chlorine atom, and a methyl group, or (3)

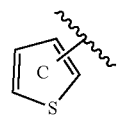

wherein
ring C is further substituted by 1 or 2 substituents selected from
(a) a C$_{3-6}$ cycloalkyl group optionally substituted by fluorine atom(s),
(b) a C$_{1-6}$ alkoxy group optionally substituted by fluorine atom(s),
(c) a C$_{3-6}$ cycloalkyloxy group optionally substituted by fluorine atom(s), and
(d) a C$_{1-2}$ alkyl group substituted by fluorine atom(s).

R$^d$ is preferably
(a) a C$_{1-6}$ alkoxy group (e.g., methoxy, ethoxy) optionally substituted by 1 to 3 fluorine atoms,
(b) a difluoromethyl group, or
(c) a trifluoromethyl group, more preferably, a C$_{1-6}$ alkoxy group (e.g., methoxy) optionally substituted by 1 to 3 fluorine atoms.

R$^{f1}$ and R$^{f2}$ are preferably each independently a hydrogen atom, a fluorine atom, or a chlorine atom, more preferably, each independently a hydrogen atom, or a fluorine atom.

R$^e$ is preferably
(a) a C$_{3-6}$ cycloalkyl group (e.g., cyclopropyl) optionally substituted by 1 to 3 fluorine atoms,
(b) a C$_{1-6}$ alkoxy group (e.g., methoxy, ethoxy) optionally substituted by 1 to 3 fluorine atoms, or
(c) a C$_{1-2}$ alkyl group (e.g., methyl, ethyl) substituted by 1-5 fluorine atoms, more preferably, a C$_{1-6}$ alkoxy group (e.g., methoxy) optionally substituted by 1 to 3 fluorine atoms.

Ring B is preferably optionally further substituted by 1 to 3 substituents selected from a fluorine atom, and a chlorine atom.

Ring C is preferably further substituted by 1 or 2 substituents selected from
(a) a C$_{3-6}$ cycloalkyl group (e.g., cyclopropyl) optionally substituted by 1 to 3 fluorine atoms, and (b) a C$_{1-2}$ alkyl group (e.g., methyl) substituted by 1 to 3 fluorine atoms.

R$^2$ is preferably (1)

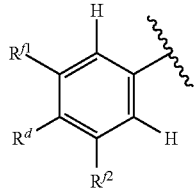

wherein each group is as defined above, or (2)

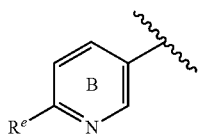

wherein each group is as defined above,
R$^d$ is preferably a C$_{1-6}$ alkoxy group (e.g., methoxy) optionally substituted by 1 to 3 fluorine atoms;
R$^{f1}$ and R$^{f2}$ are preferably each independently a hydrogen atom, or a fluorine atom;
R$^e$ is preferably a C$_{1-6}$ alkoxy group (e.g., methoxy) optionally substituted by 1 to 3 fluorine atoms;
ring B is preferably optionally further substituted by 1 to 3 substituents selected from a fluorine atom and a chlorine atom.

R$^2$ is further preferably

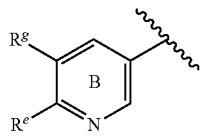

wherein R$^g$ is a fluorine atom or a chlorine atom, and R$^e$ is as defined above,
R$^g$ is preferably a fluorine atom;
R$^e$ is preferably a C$_{1-6}$ alkoxy group (preferably methoxy group) substituted by 1 to 3 fluorine atoms.

Preferable examples of compound (I) include the following compounds.

[Compound I-1]

Compound (I), wherein R$^1$ is

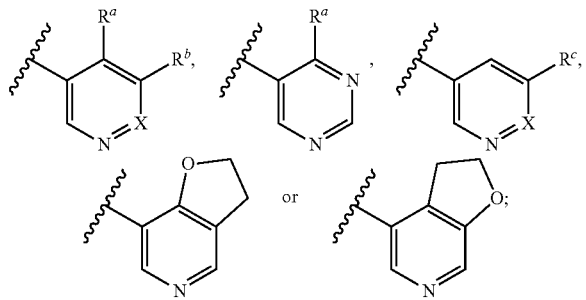

wherein
X is CH or a nitrogen atom;
R$^a$ is
(1) a C$_{1-3}$ alkyl group (e.g., methyl, ethyl) optionally substituted by 1 to 3 fluorine atoms,
(2) a C$_{3-6}$ cycloalkyl group (e.g., cyclopropyl, cyclobutyl) optionally substituted by 1 to 3 fluorine atoms,
(3) a C$_{1-6}$ alkoxy group (e.g., methoxy, ethoxy, isopropoxy) optionally substituted by 1 to 3 fluorine atoms, or
(4) a C$_{3-6}$ cycloalkyloxy group (e.g., cyclopropyloxy, cyclobutyloxy) optionally substituted by 1 to 3 fluorine atoms;
R$^b$ is
(1) a hydrogen atom, or
(2) a halogen atom (e.g., fluorine atom, chlorine atom);
R$^c$ is
(1) a C$_{1-6}$ alkoxy group (e.g., methoxy) optionally substituted by 1 to 3 fluorine atoms, or
(2) a halogen atom (e.g., chlorine atom, bromine atom);
R$^2$ is
(1)

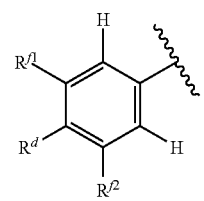

wherein
R$^d$ is
(a) a C$_{1-6}$ alkoxy group (e.g., methoxy, ethoxy) optionally substituted by 1 to 3 fluorine atoms,
(b) a difluoromethyl group, or
(c) a trifluoromethyl group; and
R$^{f1}$ and R$^{f2}$ are each independently a hydrogen atom, a fluorine atom, or a chlorine atom, (2)

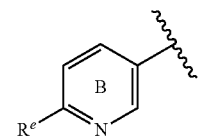

wherein
R$^e$ is
(a) a C$_{3-6}$ cycloalkyl group (e.g., cyclopropyl) optionally substituted by 1 to 3 fluorine atoms,
(b) a C$_{1-6}$ alkoxy group (e.g., methoxy, ethoxy) optionally substituted by 1 to 3 fluorine atoms, or
(c) a C$_{1-2}$ alkyl group (e.g., methyl, ethyl) substituted by 1-5 fluorine atoms; and
ring B is optionally further substituted by 1 to 3 substituents selected from a fluorine atom, and a chlorine atom, or (3)

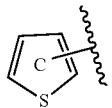

wherein
ring C is further substituted by 1 or 2 substituents selected from
(a) a $C_{3-6}$ cycloalkyl group (e.g., cyclopropyl) optionally substituted by 1 to 3 fluorine atoms, and
(b) a $C_{1-2}$ alkyl group (e.g., methyl) substituted by 1 to 3 fluorine atoms.

[Compound I-2]
Compound (1), wherein
$R^1$ is

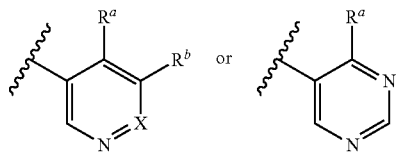

X is CH;
$R^a$ is
(1) a $C_{1-3}$ alkyl group (e.g., methyl),
(2) a $C_{1-6}$ alkoxy group (e.g., methoxy, ethoxy), or
(3) a $C_{3-6}$ cycloalkyloxy group (e.g., cyclopropyloxy);
$R^b$ is
(1) a hydrogen atom, or
(2) a halogen atom (e.g., fluorine atom);
$R^2$ is
(1)

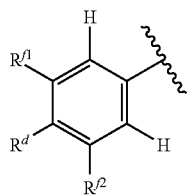

wherein
$R^d$ is a $C_{1-6}$ alkoxy group (e.g., methoxy) optionally substituted by 1 to 3 fluorine atoms;
$R^{f1}$ and $R^{f2}$ are each independently a hydrogen atom, or a fluorine atom, or
(2)

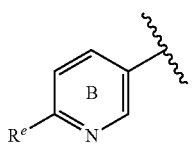

wherein
$R^e$ is a $C_{1-6}$ alkoxy group (e.g., methoxy) optionally substituted by 1 to 3 fluorine atoms; and
ring B is optionally further substituted by 1 to 3 substituents selected from a fluorine atom, and a chlorine atom.

Specific examples of compound (I) include the compounds of the below-mentioned Examples 1-124.

As a salt of a compound represented by the formula (I), a pharmacologically acceptable salt is preferable, and examples of such salt include a salt with inorganic base, a salt with organic base, a salt with inorganic acid, a salt with organic acid, and a salt with basic or acidic amino acid.

Preferable examples of the salt with inorganic base include alkali metal salts such as sodium salt, potassium salt and the like, alkaline earth metal salts such as calcium salt, magnesium salt and the like, aluminum salt, and ammonium salt.

Preferable examples of the salt with organic base include salts with trimethylamine, triethylamine, pyridine, picoline, ethanolamine, diethanolamine, triethanolamine, tromethamine [tris(hydroxymethyl)methylamine], tert-butylamine, cyclohexylamine, benzylamine, dicyclohexylamine, and N,N-dibenzylethylenediamine.

Preferable examples of the salt with inorganic acid include salts with hydrogen chloride, hydrogen bromide, nitric acid, sulfuric acid, and phosphoric acid.

Preferable examples of the salt with organic acid include salts with formic acid, acetic acid, trifluoroacetic acid, phthalic acid, fumaric acid, oxalic acid, tartaric acid, malefic acid, citric acid, succinic acid, malic acid, methanesulfonic acid, benzenesulfonic acid, and p-toluenesulfonic acid.

Preferable examples of the salt with basic amino acid include salts with arginine, lysine, and ornithine.

Preferable examples of the salt with acidic amino acid include salts with aspartic acid, and glutamic acid.

Compound (I) may be used as a prodrug.

The prodrug of compound (I) refers to a compound which is converted to compound (I) as a result of a reaction with an enzyme, gastric acid, etc. under physiological conditions in vivo, thus a compound that undergoes enzymatic oxidation, reduction, hydrolysis etc. to convert to compound (I) and a compound that undergoes hydrolysis and the like by gastric acid, etc. to convert to compound (I).

Examples of the prodrug for compound (I) include
a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, or t-butylation);
a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation);
a compound obtained by subjecting a carboxyl group in compound (I) to esterification or amidation (e.g., a compound obtained by subjecting a carboxyl group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation and the like). Any of these compounds can be produced from compound (I) according to a method known per se.

The prodrug of compound (I) may also be one which is converted to compound (I) under physiological conditions as described in "IYAKUHIN no KAIHATSU (Development of Pharmaceuticals)", Vol. 7, Design of Molecules, p. 163-198, Published by HIROKAWA SHOTEN (1990).

In the present specification, a prodrug may form a salt, and as such salt, those exemplified as a salt of the compound represented by the aforementioned formula (I) can be mentioned.

Compound (I) may be labeled with an isotope (e.g., $^3$H, $^{13}$C, $^{14}$C, $^{18}$F, $^{35}$S, $^{125}$I) and the like.

Compound (I) labeled with or substituted by an isotope can be used, for example, as a tracer used for Positron Emission Tomography (PET) (PET tracer), and can be useful in the fields of medical diagnosis and the like.

Furthermore, compound (I) may be a hydrate or a non-hydrate, or a non-solvate, or a solvate.

Compound (I) also encompasses a deuterium conversion form wherein $^1$H is converted to $^2$H(D).

Furthermore, compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, and stability). The cocrystal and cocrystal salt can be produced by cocrystallization method known per se.

Compound (I) or a prodrug thereof (hereinafter sometimes to be simply abbreviated as the compound of the present invention) can be used as it is or in the form of a pharmaceutical composition (hereinafter sometimes to be abbreviated as the "medicament of the present invention") by mixing with a pharmacologically acceptable carrier etc. to mammals (e.g., human, mouse, rat, rabbit, dog, cat, bovine, horse, swine, monkey) as an agent for the prophylaxis or treatment of various diseases mentioned below.

As pharmacologically acceptable carriers, various organic or inorganic carrier substances conventionally used as preparation materials can be used. These can be incorporated as excipient, lubricant, binder and disintegrant for solid preparations; or solvent, solubilizing agent, suspending agent, isotonicity agent, buffer and soothing agent for liquid preparations; and the like. Where necessary, preparation additives such as preservative, antioxidant, colorant, sweetening agent and the like can be used.

Preferable examples of the excipient include lactose, sucrose, D-mannitol, D-sorbitol, starch, gelatinated starch, dextrin, crystalline cellulose, low-substituted hydroxypropylcellulose, sodium carboxymethylcellulose, gum arabic, pullulan, light anhydrous silicic acid, synthetic aluminum silicate and magnesium aluminometasilicate.

Preferable examples of the lubricant include magnesium stearate, calcium stearate, talc and colloidal silica.

Preferable examples of the binder include gelatinated starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrant include lactose, sucrose, starch, carboxymethylcellulose, calcium carboxymethylcellulose, croscarmellose sodium, sodium carboxymethyl starch, light anhydrous silicic acid and low-substituted hydroxypropylcellulose.

Preferable examples of the solvent include water for injection, physiological brine, Ringer's solution, alcohol, propylene glycol, polyethylene glycol, sesame oil, corn oil, olive oil and cottonseed oil.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, lauryl aminopropionate, lecithin, benzalkonium chloride, benzethonium chloride, glycerol monostearate and the like; hydrophilic polymers such as poly(vinyl alcohol), polyvinylpyrrolidone, carboxymethylcellulose sodium, methylcellulose, hydroxymethylcellulose, hydroxyethylcellulose, hydroxypropylcellulose and the like, polysorbates; and polyoxyethylene hydrogenated castor oil.

Preferable examples of the isotonicity agent include sodium chloride, glycerol, D-mannitol, D-sorbitol and glucose.

Preferable examples of the buffer include buffers of phosphate, acetate, carbonate, citrate etc.

Preferable examples of the soothing agent include benzyl alcohol.

Preferable examples of the preservative include p-oxybenzoate esters, chlorobutanol, benzyl alcohol, phenethyl alcohol, dehydroacetic acid and sorbic acid.

Preferable examples of the antioxidant include sulfite salts and ascorbate salts.

Preferable examples of the colorant include aqueous food tar colors (e.g., food colors such as Food Color Red Nos. 2 and 3, Food Color Yellow Nos. 4 and 5, Food Color Blue Nos. 1 and 2 and the like), water insoluble lake dyes (e.g., aluminum salt of the aforementioned aqueous food tar color), natural dyes (e.g., β-carotene, chlorophyll, red iron oxide) and the like.

Preferable examples of the sweetening agent include saccharin sodium, dipotassium glycyrrhizinate, aspartame and stevia.

Examples of the dosage form of the medicament of the present invention include oral preparations such as tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, aerosol, film (e.g., orally disintegrating film, oral mucosa-adhesive film), and parenteral preparations such as injection (e.g., subcutaneous injection, intravenous injection, intramuscular injection, intraperitoneal injection, drip infusion), external preparations such as transdermal absorption type preparation, ointment, lotion, adhesive preparation, suppository (e.g., rectal suppository, vaginal suppository), pellet, nasal preparation, pulmonary preparation (inhalant), eye drop, and the like. The compound of the present invention and the medicament of present invention can be administered orally or parenterally (e.g., intravenous, intraarterial, intramuscular, subcutaneous, intraorgan, intranasal, intradermal, instillation, intracerebral, intrarectal, intravaginal, intraperitoneal and intratumor administrations, administration to the vicinity of tumor, and direct administration to the lesion).

These preparations may be a release control preparation (e.g., sustained-release microcapsule) such as an immediate-release preparation, a sustained-release preparation and the like.

The medicament of the present invention can be produced according to a method conventionally used in the field of pharmaceutical formulation, for example, the method described in the Japanese Pharmacopoeia, and the like.

While the content of the compound of the present invention in the medicament of the present invention varies depending on the dosage form, dose of the compound of the present invention and the like, it is, for example, about 0.1 to 100 wt %.

When an oral preparation is produced, coating may be applied where necessary for the purpose of taste masking, enteric solubility or sustainability.

Examples of the coating base used for coating include sugar coating base, water-soluble film coating base, enteric film coating base, and sustained-release film coating base.

As the sugar coating base, sucrose is used, and one or more kinds selected from talc, precipitated calcium carbonate, gelatin, gum arabic, pullulan, and carnauba wax may be further used in combination.

Examples of the water-soluble film coating base include cellulose polymers such as hydroxypropylcellulose, hydroxypropylmethylcellulose, hydroxyethylcellulose, methylhydroxyethylcellulose and the like; synthetic polymers such as polyvinyl acetal diethylaminoacetate, aminoalkylmethacrylate copolymer E [Eudragit E (trade name)], polyvinylpyrrolidone and the like; and polysaccharides such as pullulan and the like.

Examples of the enteric film coating base include cellulose polymers such as hydroxypropylmethylcellulose phthalate, hydroxypropylmethylcellulose acetate succinate, carboxymethylethylcellulose, cellulose acetate phthalate and the like; acrylic acid polymers such as methacrylic acid copolymer L [Eudragit L (trade name)], methacrylic acid copolymer LD [Eudragit L-30D55 (trade name)], methacrylic acid copolymer S [Eudragit S (trade name)] and the like; and naturally-occurring substances such as shellac and the like.

Examples of the sustained-release film coating base include cellulose polymers such as ethylcellulose and the like; and acrylic acid polymers such as aminoalkylmethacrylate copolymer RS [Eudragit RS (trade name)], ethyl acrylate-methyl methacrylate copolymer suspension [Eudragit NE (trade name)] and the like.

Two or more kinds of the above-mentioned coating bases may be used in a mixture at an appropriate ratio. In addition, for example, light shielding agents such as titanium oxide, and red ferric oxide may also be used during coating.

The compound of the present invention has an antagonistic action on an NMDA receptor containing the NR2B subunit. As used herein, the antagonistic action on an NMDA receptor containing the NR2B subunit is confirmed by, for example, a suppressive effect on the receptor activation (e.g., glutamic acid-induced intracellular calcium ion ($Ca^{2+}$) influx).

The NMDA receptor containing the NR2B subunit is a receptor composed of four subunits in total including one NR2B subunit, and further, three subunits of 2 or 3 kinds selected from NR1, NR2A, NR2B, NR2C, NR2D, NR3A and NR3B.

The NMDA receptor containing the NR2B subunit is preferably a receptor composed of four subunits including a heterodimer of NR1 and NR2B, and a heterodimer of NR1 and one subunit selected from NR2A, NR2B, NR2C and NR2D.

The NMDA receptor containing the NR2B subunit is more preferably a receptor composed of four subunits including 2 sets of heterodimers of NR1 and NR2B.

Since the compound of the present invention is expected to show low toxicity (e.g., cardiotoxicity, acute toxicity, chronic toxicity, genetic toxicity, reproductive toxicity, pulmonary toxicity, carcinogenicity) and less side effects (e.g., pscychotomimetic side effect), it can be used as a prophylactic or therapeutic agent, or diagnostic agent for various diseases in mammals.

The compound of the present invention is expected to show low mutagenicity in the Ames test, and low hERG (human Ether-a-go-go Related Gene) inhibitory action. In addition, the compound of the present invention is expected to show low extracerebral excretion via BCRP (Breast Cancer Resistance Protein) transporter and superior stability against conjugation metabolism.

The compound of the present invention is further expected to be superior in intracerebral transferability.

The compound of the present invention can be used as a prophylactic or therapeutic agent for central and peripheral diseases. For example, the compound of the present invention can be useful as an agent for the prophylaxis or treatment of various diseases such as (1) psychiatric diseases [e.g., major depression (including intractable major depression, treatment resistant depression), minor depressive disorder, bipolar depression, recurrent depression, postpartum depression, stress disorder, major depressive disorder concomitant with psychosis (including delusive disorders and schizophrenia), manic or mixed mood episode, hypomanic mood episode, depression episode with atypical features, depression episode with melancholic features, depressive episodes with tonic features, depression episode after stroke (the above are sometimes simply indicated as "depression" in the present specification), dysthymic disorder, emotional disorder (seasonal affective disorder and the like), delirium, peripheral symptoms of dementia (mental symptoms or behavior abnormalities), anxiety, generalized anxiety disorder, anxiety syndrome, anxiety neurosis, mood disorder, cyclothymic disorder, premenstrual dysphoric disorder, panic disorder, phobia, social phobia, social anxiety disorder, obsessive disorder, post-traumatic stress syndrome, post-traumatic stress disorder, delusions or depression-type schizoaffective disorder, delusive personality disorder, Tourette syndrome, autism, fragile X syndrome, Rett syndrome, adjustment disorder, bipolar disorder (including type I bipolar disorder and type II bipolar disorder), neurosis, schizophrenia (e.g., positive symptom, negative symptom, memory disorders, delusional schizophrenia, disorganized schizophrenia, tension type schizophrenia, undifferentiated schizophrenia, remnant type schizophrenia), schizophreniform disorder, chronic fatigue syndrome, compulsive neurosis, epilepsy, refractory epilepsy syndrome in children, West syndrome, dysphoric mental state, emotional abnormality, cyclothymia, nervous erethism, faint, addiction, low sex drive, attention deficit hyperactivity disorder (ADHD), psychotic disturbance (e.g., short-term psychotic disorder, shared psychotic disorder), psychosis induced by alcohol, amphetamine, cannabis, cocaine, hallucinogen, obesity, inhalation medicine, opioids or phencyclidine, delusional disorder, Noonan syndrome, Angelman syndrome, Prader-Willi syndrome, Beckwith-Wiedemann syndrome, Silver-Russell syndrome, tuberous sclerosis, Williams syndrome, Kallmann syndrome, Rubinstein-Taybi syndrome], movement disorder, mental retardation, paranoid tendency, (2) neurodegenerative diseases [e.g., Alzheimer's disease, Alzheimer-type senile dementia, Parkinson's disease, Huntington's disease, multi-infarct dementia, frontotemporal dementia, frontotemporal dementia Parkinson's Type, alcoholic dementia or other drug related dementia, dementia associated with intracranial tumor or brain trauma, Dementia associated with Huntington's disease or Parkinson's disease, neurodegeneration accompanying brain trauma, neurodegeneration accompanying stroke, neurodegeneration accompanying cerebral infarction, neurodegeneration associated with hypoglycemia, neurodegeneration accompanying epileptic seizures, neurodegeneration accompanying neurotoxicosis, multiple system atrophy, spinal cord injury, AIDS-related dementia, progressive supranuclear palsy, Pick's syndrome, Niemann-Pick syndrome, corticobasal degeneration, Down's syndrome, vascular dementia, postencephalitic parkinsonism, dementia with Lewy bodies, HIV dementia, amyotrophic lateral sclerosis (ALS), motor neurogenesis disease (MND), Creutzfeldt-Jakob disease or prion disease, cerebral palsy, multiple sclerosis, neuromyopathy], (3) amnestic disorder, mild cognitive impairment, learning disability (e.g., reading disturbance, arithmetic disorder, dysgraphia), age-related cognition memory disorders [e.g., age-related memory disorders, senile dementia], (4) sleep disorders [e.g., intrinsic sleep disorders (e.g., psychophysiological insomnia and the like), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome, non-24-hour sleep-wake and the like), parasomnia, sleep disorders associated with internal medical or psychiatric disorder (e.g., chronic obstructive pulmonary diseases, Alzheimer's disease, Parkinson's disease, cerebrovascular dementia, schizophrenia, depression, anxiety neurosis), stress insomnia, insomnia, insomniac neurosis, sleep apnea syndrome], (5) respiratory depression caused by anesthetics, traumatic disease, or neurodegenerative so disease and the like, (6) pain [e.g., psychogenic pain (somatoform disorder, pain disorder, somatization disorder, hypochondriasis, conversion disorder, chronic pain accompanied by depression), inflammatory pain, peripheral neuropathic pain, central neuropathic pain, neuropathic pain, acute pain, intractable pain, cancerous continuous pain, cancerous breakthrough pain, cancer pain, continuous pain, physical pain, breakthrough pain, chronic pain, tenderness, generalized pain, dull pain, dermatological pain, radiation pain, pain, postoperative thoracotomy pain syndrome], (7) deafness [e.g., kanamycin deafness, streptomycin deafness, toxic deafness, senile deafness, idiopathic bilateral sensorineural hearing loss, sudden deafness, acquired deaf mutism, genetic deafness, organic deafness, high-tone sensorineural hearing loss, occupational hearing loss, low-tone sensorineural hearing loss], (8) traumatic brain injury, and disorder or complication associated therewith, post concussive syndrome, shaken baby syndrome, cerebral apoplexy, age-related macular degeneration, oculopalatal tremor, convulsions, phantom limb pain, radiation somnolence syndrome, neurotic anorexia, eating disorder, anorexia nervosa, hyperorexia, other eating disorder, alcohol dependence, alcohol abuse, alcoholic amnesia, alcohol paranoia, alcohol preference, alcohol withdrawal, alcoholic insanity, alcohol poisoning, alcoholic jealousy, alcoholic mania, alcohol-dependent psychiatric disorder, hepatic encephalopathy, pharmacophilia, pharmacophobia, pharmacomania, drug abuse, drug dependence, drug withdrawal, migraine, stress headache, catatonic headache, diabetic neuropathy, obesity, diabetes, muscular convulsions, Meniere's disease, autonomic ataxia, alopecia, glaucoma, hypertension, cardiac disease, tachycardia, congestive cardiac failure, breathing, bronchial asthma, apnea, sudden infant death syndrome, inflammatory disease, allergic disease, systemic lupus erythematosus, impotence, climacteric disorder, infertility, cancer, immunodeficiency syndrome caused by HIV infection, immunodeficiency syndrome caused by stress, cerebrospinal meningitis, acromegaly, incontinence, metabolic syndrome, osteoporosis, peptic ulcer, irritable bowel syndrome, inflammatory bowel disease, ulcerative colitis, Crohn's disease, stress gastrointestinal disorder, nervous vomiting, diarrhea, constipation, postoperative ileus, and the like.

Particularly, the compound of the present invention can be useful for the prophylaxis or treatment of depression (including major depression, intractable major depression, treatment resistant depression and the like), bipolar disorder, migraine, pain or peripheral symptoms of dementia.

Depression and bipolar disorder are diseases showing depression state or depression state and manic state for a long term. In recent years, it has been found that single intravenous administration of ketamine, an NMDA receptor antagonist, improves depression symptom accompanying major depression and bipolar disorder rapidly and in a sustained manner (Therapeutic Advances in Psychopharmacology (Ther. Adv. Psychopharmacol.), vol. 4, pp. 75-99, 2014). It has also been reported that continuous intravenous administration of CP-101, 606, which are antagonists of NMDA receptor containing the NR2B subunit significantly improves treatment resistant-depression symptom (Journal of Clinical Psychopharmacology (J. Clin. Psychopharmacol.), vol. 28, pp. 631-637, 2008). Therefore, the compound of the present invention is promising as a prophylactic or therapeutic drug for treatment resistant-depression disease.

Migraine is a chronic and paroxysmal primary headache. While the onset mechanism is unknown, it is considered to be developed along with abnormalities of central nervous system process, abnormalities of trigeminal nerve blood vessel system and the like. In pathophysiology study of migraine, particularly aura thereof, a cortical spreading depression phenomenon is attracting attention. It has been reported that CP-101, 606 and Ro25-6981, which are antagonists of NMDA receptor containing the NR2B subunit, suppress the number of occurrence and the depth of cortical spreading depression in an experimental cortical spreading depression test using rodents (the Journal of Pharmacology and Experimental Therapeutics (J. Pharmacol. Exp. Ther.), vol. 321, pp. 564-572, 2007). Therefore, the compound of the present invention is promising as a prophylactic or therapeutic drug for migraine.

Pain is classified into acute pain whose pain lasts for a comparatively short period of time, and chronic pain accompanying retention or recurrence for 3 months or longer, retention for not less than one month after recovery of acute tissue injury, or an unhealed lesion. An NMDA receptor containing the NR2B subunit is highly expressed in posterior horn of spinal cord which plays an important role in the acceptance of pain, and functional control thereof is suggested to enable pain control. In fact, a genetic modification operation that causes functional decline of NR2B subunit has been reported to elevate the pain sense threshold (European Journal of Neuroscience (Eur. J. Neurosci.), vol. 32, pp. 798-810, 2010). Also, it has been reported that the pain sense threshold increases due to Ifenprodil as an antagonist of an NMDA receptor containing the NR2B subunit (Pain, vol. 153, pp. 1022-1029, 2012). Therefore, the compound of the present invention is promising as a prophylactic or therapeutic drug for pain.

Dementia refers to chronic, general, and generally irreversible decline of cognition. While the degradation of quality of life of patients due to the cognitive decline is remarkable, peripheral symptoms of dementia (psychological symptom or abnormal behavior) is also considered to be a factor markedly influencing the degradation of quality of life of patients and caregiver thereof. An effective therapeutic intervention method for peripheral symptoms of dementia has not been established; however, it has been reported that administration of memantine, which is an NMDA receptor antagonist, partially improves peripheral symptoms of dementia (Annals of Pharmacotherapy (Ann. Pharmacother.), vol. 42, pp. 32-38, 2007). While NMDA receptor containing the NR2B subunit is widely distributed in the brain except cerebellum, peripheral symptoms of dementia has been reported to be related to white matter abnormality of brain region except cerebellum (Journal of the Neurological Sciences (J. Neurol. Sci.), vol. 337, pp. 162-166, 2014). Therefore, the compound of the present invention is promising as a prophylactic or therapeutic drug for peripheral symptoms of dementia.

While the dose of the compound of the present invention can vary depending on the subject of administration, administration route, target disease, symptom and the like, for example, when the compound of the present invention is administered orally or parenterally to an adult patient, its dose can be, for example, generally about 0.01 to 100 mg/kg body weight per dose, preferably 0.1 to 50 mg/kg body weight per dose and more preferably 0.5 to 20 mg/kg body weight per dose. This amount is desirably administered in one to 3 portions daily.

The compound of the present invention can be used in combination with other active ingredients (hereinafter to be abbreviated as concomitant drug).

Examples of the concomitant drug include the following. Acetylcholine esterase inhibitor (e.g., donepezil, rivastigmine, galanthamine, zanapezil), antidementia agent (e.g., memantine), inhibitor of 13 amyloid protein production, secretion, accumulation, aggregation and/or deposition, β secretase inhibitor (e.g., 6-(4-biphenylyl)methoxy-2-[2-(N,N-dimethylamino)ethyl]tetralin, 6-(4-biphenylyl)methoxy-2-(N,N-dimethylamino)methyltetralin, 6-(4-biphenylyl)methoxy-2-(N,N-dipropylamino)methyltetralin, 2-(N,N-dimethylamino)methyl-6-(4'-methoxybiphenyl-4-yl) methoxytetralin, 6-(4-biphenylyl)methoxy-2-[2-(N,N-diethylamino)ethyl]tetralin, 2-[2-(N,N-dimethylamino) ethyl]-6-(4'-methylbiphenyl-4-yl)methoxytetralin, 2-[2-(N,N-dimethylamino)ethyl]-6-(4'-methoxybiphenyl-4-yl) methoxytetralin, 6-(2',4'-dimethoxybiphenyl-4-yl)methoxy-2-[2-(N,N-dimethylamino)ethyl]tetralin, 6-[4-(1,3-benzodioxol-5-yl)phenyl]methoxy-2-[2-(N,N-dimethylamino)ethyl]tetralin, 6-(3',4'-dimethoxybiphenyl-4-yl)methoxy-2-[2-(N,N-dimethylamino)ethyl]tetralin, an optically active form thereof, a salt thereof and a hydrate thereof, OM99-2 (WO01/00663)), γ secretase inhibitor, β amyloid protein aggregation inhibitor (e.g., PTI-00703, ALZHEMED (NC-531), PPI-368 (Japanese National Publication of so International Patent Application No. 11-514333), PPI-558 (Japanese National Publication of International Patent Application No. 2001-500852), SKF-74652 (Biochem. J. (1999), 340(1), 283-289)), β amyloid vaccine, β amyloid-degrading enzyme and the like, brain function enhancer (e.g., aniracetam, nicergoline), therapeutic drug for Parkinson's disease [(e.g., dopamine receptor agonist (e.g., L-DOPA, bromocriptine, pergolide, talipexole, pramipexole, cabergoline, amantadine), monoamine oxidase enzyme (MAO) inhibitor (e.g., deprenyl, selegiline, remacemide, riluzole), anticholinergic agent (e.g., trihexyphenidyl, biperiden), COMT inhibitor (e.g., entacapone)], therapeutic drug for amyotrophic lateral sclerosis (e.g., riluzole etc., neurotrophic factor), therapeutic drug for abnormal behavior, wandering and the like accompanying progress of dementia (e.g., sedative, anti-anxiety drug), apoptosis inhibitor (e.g., CPI-1189, IDN-6556, CEP-1347), neuronal differentiation/regeneration promoter (e.g., leteprinim, xaliproden; SR-57746-A), SB-216763, Y-128, VX-853, prosaptide, 5,6-dimethoxy-2-[2,2,4,6,7-pentamethyl-3-(4-methylphenyl)-2,3-dihydro-1-benzofuran-5-yl]isoindoline, 5,6-dimethoxy-2-[3-(4-isopropylphenyl)-2,2,4,6,7-pentamethyl-2,3-dihydro-1-benzofuran-5-yl]isoindoline, 6-[3-(4-isopropylphenyl)-2,2,4,6,7-pentamethyl-2,3-dihydro-1-benzofuran-5-yl]-6,7-dihydro-5H-[1,3]dioxolo[4,5-f]isoindole and an optically active form, salt or hydrate thereof), non-steroidal antiinflammatory agents (meloxicam, tenoxicam, indomethacin, ibuprofen, celecoxib, rofecoxib, aspirin, indomethacin etc.), steroid drug (dexamethasone, hexestrol, cortisone acetate etc.), disease-modifying anti-rheumatic drug (DMARDs), anti-cytokine drug (e.g., TNF inhibitor, MAP kinase inhibitor), therapeutic agent for incontinence, frequent urination (e.g., flavoxate hydrochloride, oxybutynin hydrochloride, propiverine hydrochloride), phosphodiesterase inhibitor (e.g., sildenafil(citrate)), dopamine agonist (e.g., apomorphine), antiarrhythmic drugs (e.g., mexiletine), sex hormone or a derivative thereof (e.g., progesterone, estradiol, estradiol benzoate), therapeutic agent for osteoporosis (e.g., alfacalcidol, calcitriol, elcatonin, calcitonin salmon, estriol, ipriflavone, pamidronate disodium, alendronate sodium hydrate, incadronate disodium), parathyroid hormone (PTH), calcium receptor antagonists, therapeutic drug for insomnia (e.g., benzodiazepines medicament, non-benzodiazepines medicament, melatonin agonist, orexin receptor antagonists), therapeutic drug for schizophrenia (e.g., typical antipsychotic agents such as haloperidol and the like; atypical antipsychotic agents such as clozapine, olanzapine, risperidone, aripiprazole and the like; medicament acting on metabotropic glutamate receptor or ion channel conjugated-type glutamate receptor; phosphodiesterase inhibitor), benzodiazepines medicament (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, clomipramine hydrochloride, mianserin hydrochloride, setiptiline maleate etc.), selective serotonin reuptake inhibitor (fluvoxamine maleate, fluoxetine hydrochloride, citalopram hydrobromide, escitalopram oxalate, sertraline hydrochloride, paroxetine hydrochloride hydrate etc.), serotonin-noradrenaline reuptake inhibitor (venlafaxine hydrochloride, duloxetine hydrochloride, desvenlafaxine etc.), noradrenaline reuptake inhibitor (reboxetine mesylate etc.), mirtazapine, trazodone hydrochloride, bupropion hydrochloride, 5-$HT_{1A}$ agonist (buspirone hydrochloride, tandospirone citrate, osemozotan hydrocloride etc.), 5-$HT_{2A}$ antagonist, 5-$HT_{2A}$ inverse agonist, 5-$HT_3$ antagonist (cyamemazine etc.), heart non-selective β inhibitor (propranolol hydrochloride, oxprenolol hydrochloride etc.), histamine $H_1$ antagonist, CRF antagonist, other antianxiety drug (meprobamate etc.), tachykinin antagonist, medicament that acts on metabotropic glutamate receptor, CCK antagonist, β3 adrenaline antagonist (amibegron hydrochloride etc.), GAT-1 inhibitor, N-type calcium channel inhibitor, carbonic anhydrase II inhibitor, NMDA glycine moiety agonist, NMDA antagonist (memantine, ketamine, esketamine, etc.), peripheral benzodiazepine receptor agonist, vasopressin receptor antagonist, phosphodiesterase inhibitor, opioid antagonist, opioid agonist, uridine, nicotinic acid receptor agonist, thyroid hormone, thyroid-stimulating hormone (TSH), thyroid-stimulating hormone release hormone (TRH), MAO inhibitor (phenelzine sulfate, tranylcypromine sulfate, moclobemide etc.), therapeutic drug for bipolar disorder (lithium carbonate, sodium valproate, lamotrigine, riluzole, felbamate etc.), cannabinoid CB1 antagonist, FAAH inhibitor, sodium channel inhibitor, anti-ADHD drug (methylphenidate hydrochloride, methamphetamine hydrochloride etc.), therapeutic drug for alcoholism, therapeutic drug for autism, therapeutic drug for chronic fatigue syndrome, therapeutic drug for spasm, therapeutic drug for fibromyalgia syndrome, therapeutic drug for headache, therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related syndrome, therapeutic drug for irritable bowel syndrome, therapeutic drug for lipid abnormality such as cholesterol-lowering drug (statins etc., fibrate, squalene synthetase inhibitor), therapeutic drug for abnormal behavior or suppressant of dromomania due to dementia (sedatives, anti-anxiety drug etc.), antiobesity drug, therapeutic drug for diabetes, therapeutic agent for diabetic complications, therapeutic drug for hypertension, therapeutic drug for hypotension, diuretic, chemotherapeutic agent, immunotherapeutic agent, antithrombotic agent, anti-cancer agent, antibody medicament, nucleic acid or nucleic acid derivative, aptamer drug and the like.

Two or more kinds of the above-mentioned concomitant drugs may be used in combination at an appropriate ratio.

When the compound of the present invention is applied to each of the above-mentioned diseases, it can also be used in combination with biologics (e.g., antibody medicament, nucleic acid or nucleic acid derivative, aptamer medicament, vaccine preparation), or can be used in combination with a gene therapy method and the like, or can also be used in combination with a treatment method in psychiatric field without using drugs.

Examples of the treatment method in the psychiatric field without using drug include modified electroconvulsive therapy, deep brain stimulation therapy, repetitive transcranial magnetic stimulation therapy, psychotherapy including cognitive behavioral therapy and the like.

The compound of the present invention can also be used in combination with various organ regeneration methods such as cardiac regeneration, renal regeneration, pancreatic regeneration, revascularization and the like, cell transplantation therapy utilizing bone marrow cells (bone marrow-derived mononuclear cell, myelogenic stem cell), or artificial organ utilizing tissue engineering (e.g., artificial blood vessel, cardiomyocyte sheet).

By combining the compound of the present invention and a concomitant drug, a superior effect such as
(1) the dose can be reduced as compared to single administration of the compound of the present invention or a concomitant drug,
(2) the drug to be combined with the compound of the present invention can be selected according to the condition of patients (mild case, severe case and the like),
(3) the period of treatment can be set longer by selecting a concomitant drug having different action and mechanism from the compound of the present invention,
(4) a sustained treatment effect can be designed by selecting a concomitant drug having different action and mechanism from the compound of the present invention,
(5) a synergistic effect can be afforded by a combined use of the compound of the present invention and a concomitant drug, and the like, can be achieved.

Hereinafter the compound of the present invention and a concomitant drug used in combination are referred to as the "combination agent of the present invention".

When using the combination agent of the present invention, the administration time of the compound of the present invention and the concomitant drug is not restricted, and the compound of the present invention or a pharmaceutical composition thereof and the concomitant drug or a pharmaceutical composition thereof may be administered to an administration subject simultaneously (the compound of the present invention and the concomitant drug may form a single preparation, or difference preparations), or may be administered at different times. When administering with a time lag, the order of administration of the compound of the present invention and the concomitant drug may be any. Also, the compound of the present invention may be administered after continuously administering the concomitant drug for a certain period.

The dosage of the concomitant drug may be determined according to the dose clinically used, and can be appropriately selected depending on an administration subject, administration route, disease, combination and the like.

The dosage of the concomitant drug can be appropriately determined based on the dose employed in clinical situations. The mixing ratio of the compound of the present invention and a concomitant drug can be appropriately determined depending on the administration subject, administration route, target disease, symptom, combination and the like.

The production method of the compound of the present invention is explained in the following.

The starting materials and reagents used in each step in the following production method, and the obtained compounds each may form a salt. Examples of the salt include those similar to the aforementioned salts of the compound of the present invention and the like.

When the compound obtained in each step is a free compound, it can be converted to a desired salt by a method known per se. Conversely, when the compound obtained in each step is a salt, it can be converted to a free form or a desired other kind of salt by a method known per se.

The compound obtained in each step can also be used for the next reaction as a reaction mixture thereof or after obtaining a crude product thereof. Alternatively, the compound obtained in each step can be isolated and/or purified from the reaction mixture by a separation means such as concentration, crystallization, recrystallization, distillation, solvent extraction, fractionation, chromatography and the like according to a conventional method.

When the starting materials and reagent compounds of each step are commercially available, the commercially available products can be used as they are.

In the reaction of each step, while the reaction time varies depending on the reagents and solvents to be used, unless otherwise specified, it is generally 1 min-48 hr, preferably 10 min-8 hr.

In the reaction of each step, while the reaction temperature varies depending on the reagents and solvents to be used, unless otherwise specified, it is generally −78° C. to 300° C., preferably −78° C. to 150° C.

In the reaction of each step, while the pressure varies depending on the reagents and solvents to be used, unless otherwise specified, it is generally 1 atm-20 atm, preferably 1 atm-3 atm.

In the reaction of each step, for example, microwave synthesizers such as Initiator manufactured by Biotage and the like are sometimes used. While the reaction temperature varies depending on the reagents and solvents to be used, unless otherwise specified, it is generally room temperature −300° C., preferably 50° C.-250° C. While the reaction time varies depending on the reagents and solvents to be used, unless otherwise specified, it is generally 1 min-48 hr, preferably 1 min-8 hr.

In the reaction of each step, unless otherwise specified, a reagent is used in 0.5 equivalent-20 equivalents, preferably 0.8 equivalent-5 equivalents, relative to the substrate. When a reagent is used as a catalyst, the reagent is used in 0.001 equivalent-1 equivalent, preferably 0.01 equivalent-0.2 equivalent, relative to the substrate. When the reagent is also a reaction solvent, the reagent is used in a solvent amount.

In the reaction of each step, unless otherwise specified, it is performed without solvent or by dissolving or suspending in a suitable solvent. Specific examples of the solvent include those described in Examples and the following.

alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
acid anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like; and
water.

Two or more kinds of the above-mentioned solvents may be used by mixing at an appropriate ratio.

When a base is used in the reaction of each step, for example, bases shown below or those described in Examples are used.

inorganic bases: sodium hydroxide, magnesium hydroxide, sodium carbonate, calcium carbonate, sodium hydrogen carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like;
metal amides: sodium amide, lithium diisopropyl amide, lithium hexamethyl disilazide and the like; and
organic lithiums: n-butyllithium and the like.

When an acid or acidic catalyst is used in the reaction of each step, for example, acids and acidic catalysts shown below or those described in Examples are used.

inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like; and
Lewis acids: boron trifluoride diethyl ether complex, zinc iodide, anhydrous aluminum chloride, anhydrous zinc chloride, anhydrous iron chloride and the like.

Unless otherwise specified, the reaction of each step is performed according to a method known per se, for example, the methods described in Jikken Kagaku Kouza 5th edition, vol. 13-vol. 19 (The Chemical Society of Japan ed.); Shinjikken Kagaku Kouza (Courses in Experimental Chemistry), vol. 14-vol. 15 (The Chemical Society of Japan ed.); Fine Organic Chemistry rev. 2nd edition (L. F. Tietze, Th. Eicher, NANKODO); rev. Organic Name Reactions, Their Mechanism and Essence (Hideo Togo, Kodansha); ORGANIC SYNTHESES Collective Volume I-VII (John Wiley & Sons Inc); Modern Organic Synthesis in the Laboratory, A Collection of Standard Experimental Procedures (Jie Jack Li, OXFORD UNIVERSITY); Comprehensive Heterocyclic Chemistry III, Vol. 1-Vol. 14 (Elsevier Japan so KK); Strategic Applications of Named Reactions in Organic Synthesis (translation supervisor Kiyoshi Tomioka, KAGAKUDOJIN); Comprehensive Organic Transformations (VCH Publishers Inc.), 1989 and the like, or the methods described in the Examples.

In each step, protection or deprotection reaction of a functional group is performed by the method known per se, for example, the methods described in "Protective Groups in Organic Synthesis, 4th Ed." (Theodora W. Greene, Peter G. M. Wuts) Wiley-Interscience, 2007; "Protecting Groups 3rd Ed." (P. J. Kocienski) Thieme, 2004 and the like, or the methods described in the Examples.

Examples of the protecting group of the hydroxyl group of alcohol and the like and a phenolic hydroxyl group include ether protecting groups such as methoxymethyl ether, benzyl ether, tert-butyldimethylsilyl ether, tetrahydropyranyl ether and the like; carboxylate ester protecting groups such as acetate ester and the like; sulfonate ester protecting groups such as methanesulfonate ester and the like; carbonate ester protecting groups such as tert-butylcarbonate and the like, and the like.

Examples of the protecting group of the carbonyl group of aldehyde include acetal protecting groups such as dimethyl acetal and the like; cyclic acetal protecting groups such as 1,3-dioxane and the like, and the like.

Examples of the protecting group of the carbonyl group of ketone include ketal protecting groups such as dimethyl ketal and the like; cyclic ketal protecting groups such as 1,3-dioxane and the like; oxime protecting groups such as O-methyloxime and the like; hydrazone protecting groups such as N,N-dimethylhydrazone and the like, and the like.

Examples of the carboxyl protecting group include ester protecting groups such as methyl ester and the like; amide protecting groups such as N,N-dimethylamide and the like, and the like.

Examples of the thiol protecting group include ether protecting groups such as benzyl thioether and the like; ester protecting groups such as thioacetate ester, thiocarbonate, thiocarbamate and the like, and the like.

Examples of the protecting group of an amino group and an aromatic hetero ring such as imidazole, pyrrole, indole and the like include carbamate protecting groups such as benzyl carbamate and the like; amide protecting groups such as acetamide and the like; alkylamine protecting groups such as N-triphenylmethylamine and the like, sulfonamide protecting groups such as methanesulfonamide and the like, and the like.

The protecting group can be removed by a method known per se, for example, a method using acid, base, ultraviolet light, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide), a reduction method and the like.

When a reduction reaction is performed in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid, triethylsilane and the like. When a carbon-carbon double bond or triple bond is reduced, a method using a catalyst such as palladium-carbon, Lindlar catalyst and the like is used.

When an oxidation reaction is performed in each step, examples of an oxidant to be used include peracids such as m-chloroperbenzoic acid (mCPBA), hydrogen peroxide, tert-butyl hydroperoxide and the like; perchlorates such as tetrabutylammonium perchlorate and the like; chlorates such as sodium chlorate and the like; chlorites such as sodium chlorite and the like; periodic acids such as sodium periodate and the like; high valent iodine reagents such as iodosylbenzene and the like; reagents containing manganese such as manganese dioxide, potassium permanganate and the like; leads such as lead tetraacetate and the like; reagents containing chrome such as pyridinium chlorochromate (PCC), pyridinium dichromate (PDC), Jones reagent and the like; halogen compounds such as N-bromosuccinimide (NBS) and the like; oxygen; ozone; sulfur trioxide pyridine complex; osmium tetraoxide; selenium dioxide; 2,3-dichloro-5,6-dicyano-1,4-benzoquinone (DDQ) and the like.

When a radical cyclization reaction is performed in each step, examples of the radical initiator to be used include azo compounds such as azobisisobutyronitrile (AIBN) and the like; water-soluble radical initiators such as 4,4'-azobis-4-cyanopentanoic acid (ACPA) and the like; triethylboron in the presence of air or oxygen; benzoyl peroxide and the like. In addition, examples of the radical reaction agent to be used include tributylstannane, tristrimethylsilylsilane, 1,1,2,2-tetraphenyldisilane, diphenylsilane, samarium iodide and the like.

When the Wittig reaction is performed in each step, examples of the Wittig reagent to be used include alkylidenephosphoranes and the like. Alkylidenephosphoranes can be prepared by a method known per se, for example, by reacting a phosphonium salt with a strong base.

When the Horner-Emmons reaction is performed in each step, examples of the reagent to be used include phosphonoacetic acid esters such as methyl dimethylphosphonoacetate, ethyl diethylphosphonoacetate and the like; and bases such as alkali metal hydrides, organic lithiums and the like.

When the Friedel-Crafts reaction is performed in each step, examples of the reagent to be used include a combination of Lewis acid and acid chloride or a combination of Lewis acid and an alkylating agent (e.g., alkyl halides, alcohol, olefins and the like). Alternatively, an organic acid and an inorganic acid can also be used instead of the Lewis acid, and acid anhydride such as acetic anhydride and the like can also be used instead of acid chloride.

When an aromatic nucleophilic substitution reaction is performed in each step, a nucleophilic agent (e.g., amines, imidazole and the like) and a base (e.g., organic bases and the like) are used as the reagent.

When a nucleophilic addition reaction with carbanion, a nucleophilic 1,4-addition reaction with carbanion (Michael addition reaction) or a nucleophilic substitution reaction with carbanion is performed in each step, examples of the base to be used for developing carbanion include organic lithiums, metal alkoxides, inorganic bases, organic bases and the like.

When the Grignard reaction is performed in each step, examples of the Grignard reagent include aryl magnesium halides such as phenyl magnesium bromide and the like; and alkyl magnesium halides such as methyl magnesium bromide and the like. The Grignard reagent can be prepared by a method known per se, for example, by reacting alkyl halide or aryl halide with metal magnesium in ether or tetrahydrofuran as a solvent.

When the Knoevenagel condensation reaction is performed in each step, an active methylene compound held between two electron-withdrawing groups (e.g., malonic acid, diethyl malonate, malononitrile and the like) and a base (e.g., organic bases, metal alkoxides, inorganic bases) are used as the reagents.

When the Vilsmeier-Haack reaction is performed in each step, phosphoryl chloride and an amide derivative (e.g., N,N-dimethylformamide and the like) are used as the reagents.

When an azidation reaction of alcohols, alkyl halides or sulfonate esters is performed in each step, examples of the azidation agent to be used include diphenylphosphoryl azide (DPPA), trimethylsilyl azide, sodium azide and the like. For example, when alcohols are azidated, a method using diphenylphosphoryl azide and 1,8-diazabicyclo[5,4,0]undec-7-ene (DBU), a method using trimethylsilyl azide and the Lewis acid and the like can be employed.

When a reductive amination reaction is performed in each step, examples of the reducing agent to be used include sodium triacetoxyborohydride, sodium cyanoborohydride, hydrogen, formic acid and the like. When the substrate is an amine compound, examples of the carbonyl compound to be used besides para-formaldehyde include aldehydes such as acetaldehyde and the like, ketones such as cyclohexanone and the like. When the substrate is a carbonyl compound, examples of the amines to be used include ammonia, primary amines such as methylamine and the like; secondary amines such as dimethylamine and the like, and the like.

When the Mitsunobu reaction is performed in each step, azodicarboxylate esters (e.g., diethyl azodicarboxylate (DEAD), diisopropyl azodicarboxylate (DIAD) and the like) and phosphines such as triphenylphosphine, tributylphosphine and the like are used as the reagents.

When an esterification reaction, amidation reaction or ureation reaction is performed in each step, examples of the reagent to be used include halogenated acyl forms such as acid chloride, acid bromide and the like; and activated carboxylic acids such as acid anhydride, active ester form, sulfuric acid ester form and the like. Examples of the carboxylic acid activator include carbodiimide condensing agents such as N-(3-(dimethylamino)propyl)-N'-ethylcarbodiimide hydrochloride (WSC·HCl) and the like; triazine condensing agents such as 4-(4,6-dimethoxy-1,3,5-triazin-2-yl)-4-methylmorpholinium chloride-n-hydrate (DMT-MM) and the like; carbonate ester condensing agents such as 1,1-carbonyldiimidazole (CDI) and the like; diphenylphosphoryl azide (DPPA); benzotriazol-1-yloxy-trisdimethyl fun inophosphonium salt (BOP reagent); 2-chloro-1-methylpyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphate (HATU); sulfuric acid; a combination thereof and the like. When a carbodiimide condensing agent is used, additives such as 1-hydroxybenzotriazole (HOBt), N-hydroxysuccinimide (HOSu), dimethylaminopyridine (DMAP) and the like can be further added to the reaction.

When a coupling reaction is performed in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride, and the like; nickel compounds such as tetrakis(triphenylphosphine)nickel(0) and the like; rhodium compounds such as tris(triphenylphosphine)rhodium(III) chloride and the like; a cobalt compound; copper compounds such as copper oxide, copper(I) iodide and the like; a platinum compound and the like. A base may be further added to the reaction and examples of such base include inorganic bases, and the like.

When a thiocarbonylation reaction is performed in each step, diphosphorus pentasulfide is representatively used as a thiocarbonylating agent. Besides diphosphorus pentasulfide, a reagent having a 1,3,2,4-dithiadiphosphetane-2,4-disulfide structure such as 2,4-bis(4-methoxyphenyl)-1,3,2,4-dithiadiphosphetane-2,4-disulfide (Lawesson reagent) and the like may also be used.

When the Wohl-Ziegler reaction is performed in each step, examples of the halogenating agent to be used include N-iodosuccinimide, N-bromosuccinimide (NBS), N-chlorosuccinimide (NCS), bromine, sulfuryl chloride and the like. Furthermore, the reaction can be accelerated by adding heat, light, radical initiators such as benzoyl peroxide, azobisisobutyronitrile and the like to the reaction.

When a halogenating reaction of a hydroxy group is performed in each step, examples of the halogenating agent to be used include acid halide of hydrohalic acid and inorganic acid; specifically, hydrochloric acid, thionyl chloride, phosphorus oxychloride and the like for chlorination, and 48% hydrobromic acid and the like for bromination. In addition, a method of obtaining a halogenated alkyl form from alcohol by reacting with triphenylphosphine and carbon tetrachloride or carbon tetrabromide, and the like may be used. Alternatively, a method of synthesizing a halogenated alkyl form via a two-step reaction including conversion of alcohol to sulfonic acid ester, and reacting same with lithium bromide, lithium chloride or sodium iodide may also be used.

When the Arbuzov reaction is performed in each step, examples of the reagent to be used include alkyl halides such as ethyl bromoacetate and the like; and phosphites such as triethylphosphite, tri(isopropyl)phosphite and the like.

When a sulfonate esterification reaction is performed in each step, examples of the sulfonylating agent to be used include methanesulfonyl chloride, p-toluenesulfonyl chloride, methanesulfonic anhydride, p-toluenesulfonic anhydride and the like.

When a hydrolysis reaction is performed in each step, an acid or a base is used as the reagent. In addition, when an acid hydrolysis reaction of tert-butyl ester is performed, formic acid, triethylsilane and the like are sometimes added to reductively trap the by-produced tert-butyl cation.

When a dehydrating reaction is performed in each step, examples of the dehydrating agent to be used include sulfuric acid, phosphorus pentaoxide, phosphorus oxychloride, N,N'-dicyclohexylcarbodiimide, alumina, polyphosphoric acid and the like.

The starting compounds used in the following respective production steps can be produced by a method known per se.

Compound (I) can be produced from compound (1) by the following Production step A.

[Production Step A]

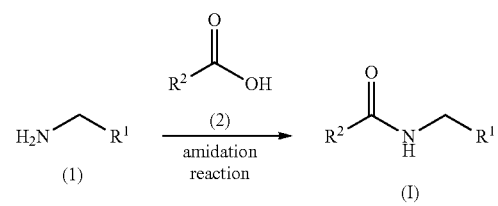

wherein $R^1$ and $R^2$ are as defined above.

Compound (I) can be produced by an amidation reaction of compound (1) with compound (2).

Compound (1) can be produced by the following Production steps B-I or a method analogous thereto.

Compound (2) can be produced by a production method known per se.

Among compounds (1), compound (1-i) can be produced from compound (3) according to the following Production step B.

[Production Step B]

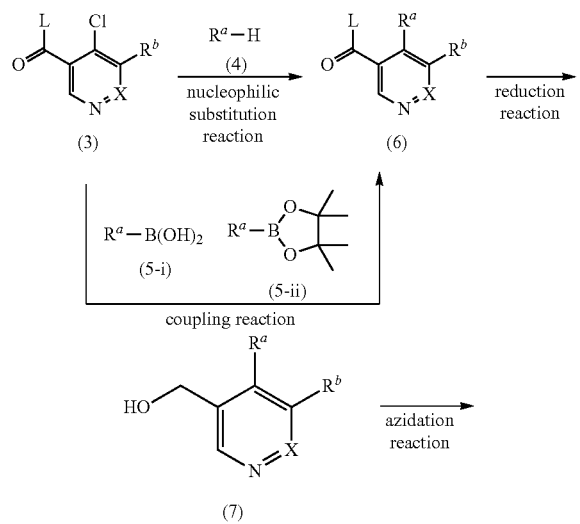

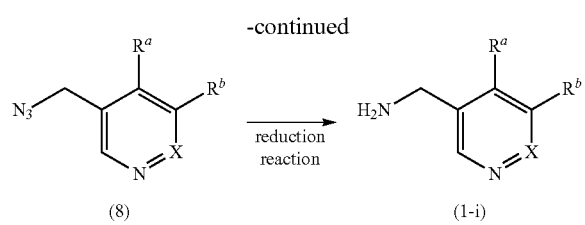

wherein L is a hydrogen atom, a hydroxyl group or a $C_{1-6}$ alkoxy group, and X, $R^a$, and $R^b$ are as defined above.

Compound (6) can be produced by subjecting compound (3) to a nucleophilic substitution reaction together with compound (4). Compound (6) can also be produced by subjecting compound (3) to a coupling reaction together with compound (5-i) or compound (5-ii). Compound (7) can be produced by subjecting compound (6) to a reduction reaction. Compound (8) can be produced by subjecting compound (7) to an azidation reaction. Compound (1-i) can be produced by subjecting compound (8) to a reduction reaction. As the reagent to be used, triphenylphosphine and the like can be mentioned.

In addition, compound (1-i) can also be produced from compound (9) according to the following Production step C.

[Production Step C]

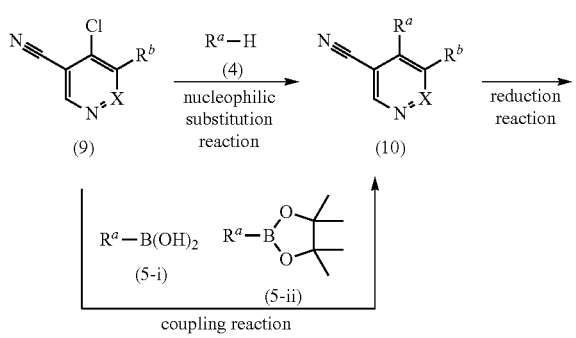

wherein X, $R^a$ and $R^b$ are as defined above.

Compound (10) can be produced by subjecting compound (9) to a nucleophilic substitution reaction together with compound (4). Compound (10) can also be produced by subjecting compound (9) to a coupling reaction together with compound (5-i) or compound (5-ii). Compound (1-i) can be produced by subjecting compound (10) to a reduction reaction. As the reagent to be used, Raney (registered trade mark) nickel, cobalt(II) chloride hydrate and the like can be mentioned.

Among compounds (1), compound (1-ii) can be produced from compound (11) according to the following Production step D.

[Production Step D]

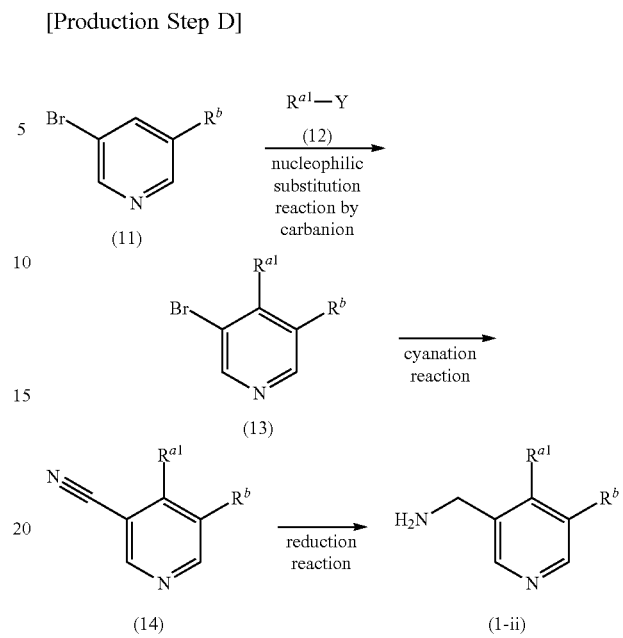

wherein Y is a halogen atom, $R^{a1}$ is a $C_{1-3}$ alkyl group optionally substituted by fluorine atom(s), and $R^b$ is as defined above.

Compound (13) can be produced by subjecting compound (11) to a nucleophilic substitution reaction by carbanion with compound (12). Compound (14) can be produced by subjecting compound (13) to a cyanation reaction. As the cyanation reagent to be used, zinc cyanide and the like can be mentioned. As the metal catalyst to be used, tetrakis (triphenylphosphine)palladium(0) and the like can be mentioned. Compound (1-ii) can be produced by subjecting compound (14) to a reduction reaction.

Among compounds (1), compound (1-iii) can be produced from compound (15) according to the following Production step E.

[Production Step E]

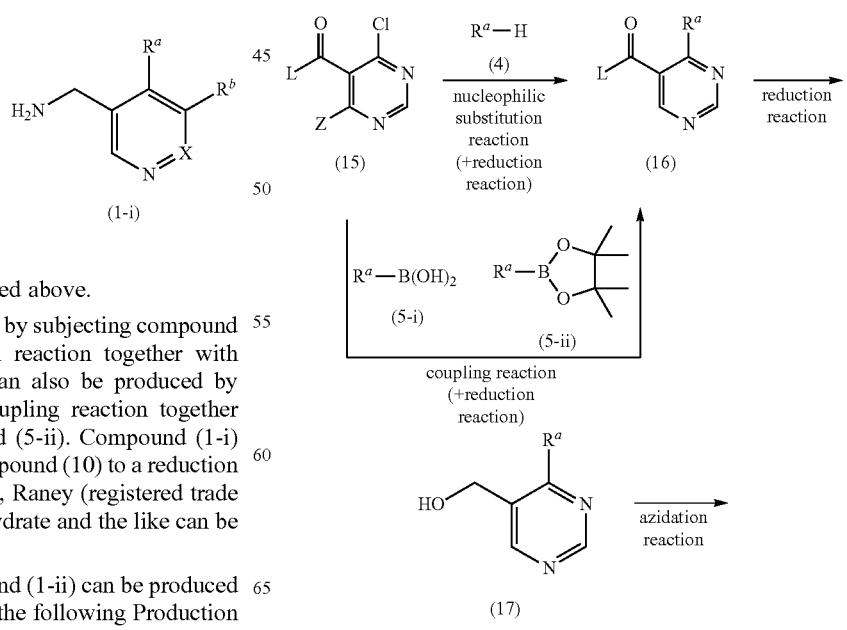

-continued

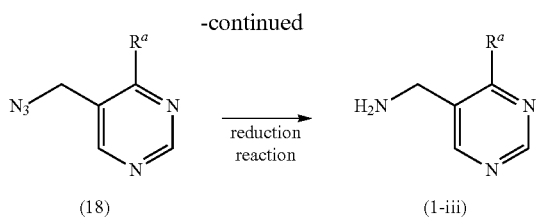

wherein L is a hydrogen atom, a hydroxyl group or a $C_{1-6}$ alkoxy group, Z is a hydrogen atom or a chlorine atom, and $R^8$ is as defined above.

When Z is a hydrogen atom, compound (16) can be produced by subjecting compound (15) to a nucleophilic substitution reaction together with compound (4). Compound (16) can also be produced by subjecting compound (15) to a coupling reaction together with compound (5-i) or compound (5-ii). When Z is a chlorine atom, compound (16) can be produced by a nucleophilic substitution reaction of compound (15) and compound (4), followed by a reduction reaction, or a coupling reaction of compound (15) and compound (5-i) or compound (5-ii), followed by a reduction reaction. Compound (17) can be produced by a reduction reaction of compound (16). Compound (18) can be produced by subjecting compound (17) to an azidation reaction. Compound (1-iii) can be produced by subjecting compound (18) to a reduction reaction.

Also, compound (1-iii) can also be produced from compound (19) according to the following Production step F.

[Production Step F]

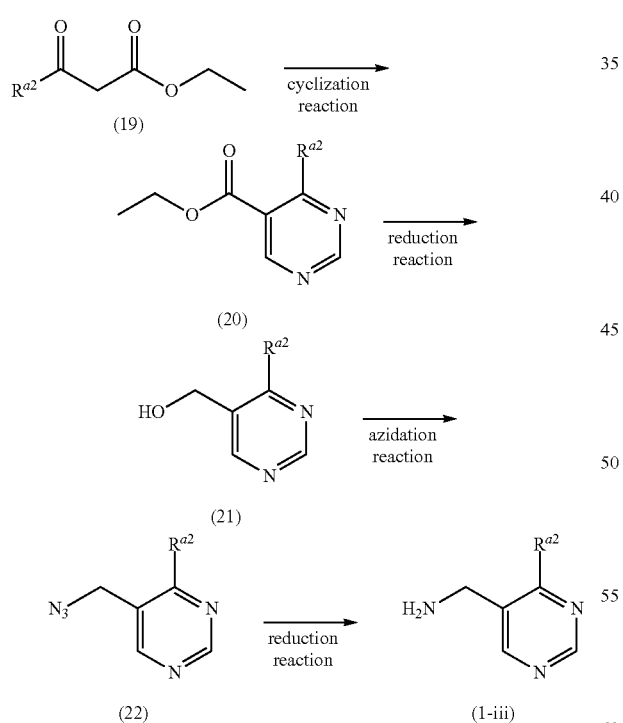

wherein $R^{a2}$ is a $C_{1-3}$ alkyl group optionally substituted by fluorine atom(s) or a $C_{3-6}$ cycloalkyl group optionally substituted by fluorine atom(s).

Compound (20) can be produced by subjecting compound (19) to cyclization reaction using formamidine hydrochloride. Compound (21) can be produced by subjecting compound (20) to a reduction reaction. Compound (22) can be produced by subjecting compound (21) to an azidation reaction. Compound (1-iii) can be produced by subjecting compound (22) to a reduction reaction.

Among compounds (1), compound (1-iv) can be produced from compound (23) according to the following Production step G.

[Production Step G]

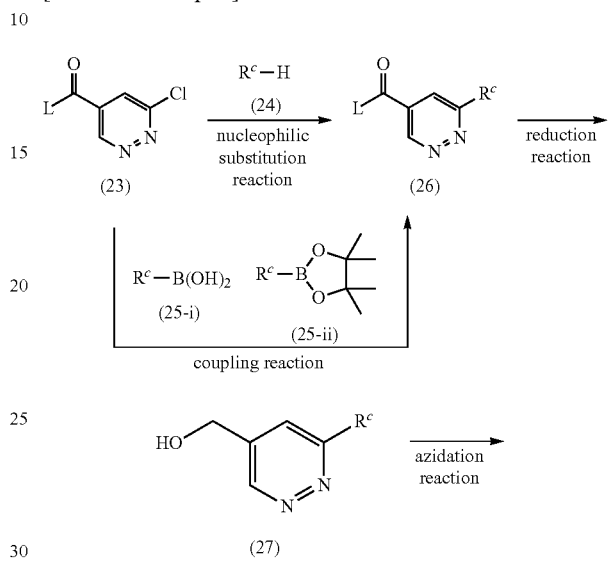

wherein L is a hydrogen atom, a hydroxyl group or a $C_{1-6}$ alkoxy group, and R is as defined above.

Compound (26) can be produced by subjecting compound (23) to a nucleophilic substitution reaction together with compound (24). Compound (26) can also be produced by subjecting compound (23) to a coupling reaction together with compound (25-i) or compound (25-ii). Compound (27) can be produced by subjecting compound (26) to a reduction reaction. Compound (28) can be produced by subjecting compound (27) to an azidation reaction. Compound (1-iv) can be produced by subjecting compound (28) to a reduction reaction.

Among compounds (1), compound (1-v) can be produced by a production method similar to Production step D.

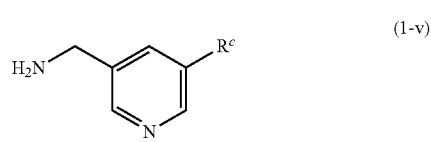

wherein $R^c$ is as defined above.

Among compounds (1), compound (1-vi) can be produced from compound (29) according to the following Production step H.

[Production Step H]

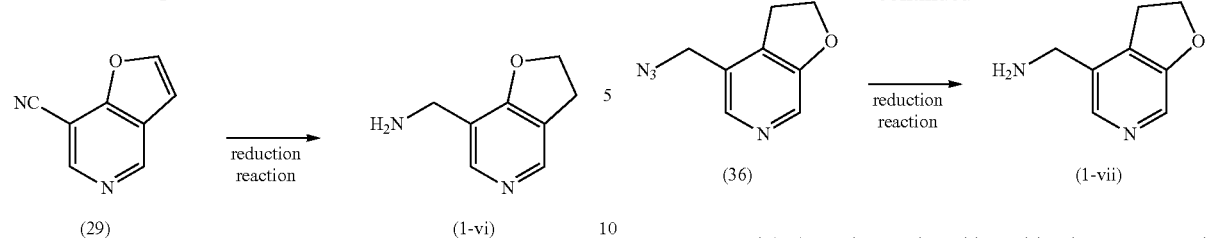

Compound (1-vi) can be produced by subjecting compound (29) to a reduction reaction.

Among compounds (1), compound (1-vii) can be produced from compound (30) according to the following Production step I.

[Production Step I]

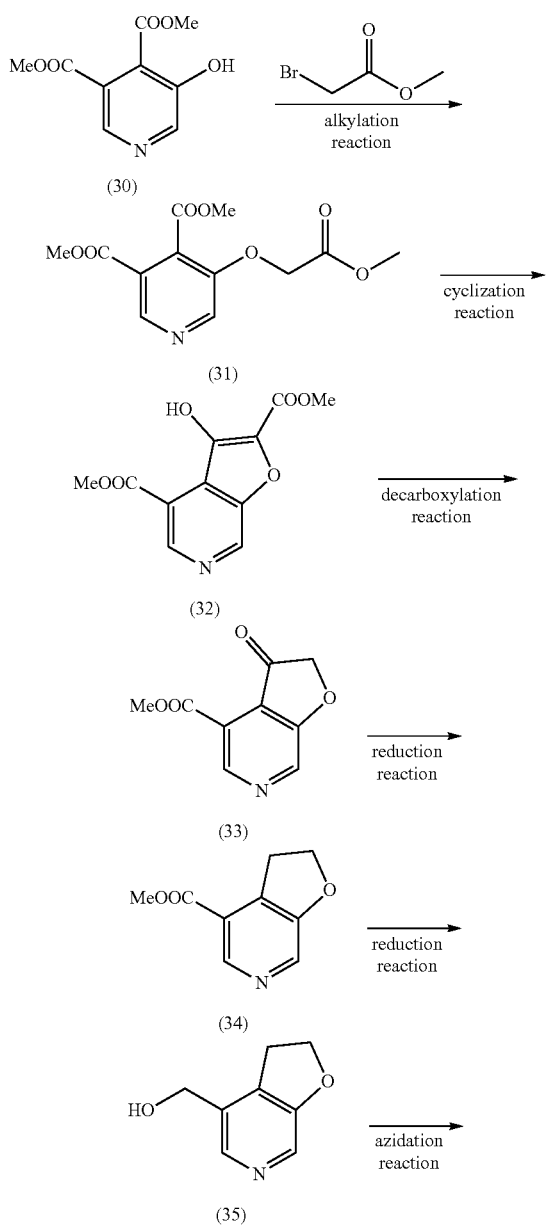

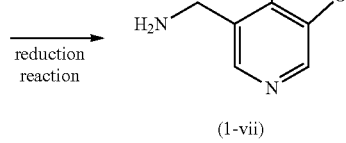

Compound (31) can be produced by subjecting compound (30) to an alkylation reaction together with methyl bromoacetate. Compound (32) can be produced by subjecting compound (31) to a cyclization reaction. As the base to be used for the cyclization reaction, sodium methoxide and the like can be mentioned. Compound (33) can be produced by subjecting compound (32) to a decarboxylation reaction. As the reagent to be used for the decarboxylation reaction, hydrochloric acid, sodium hydroxide, lithium hydroxide and the like can be mentioned. Compound (34) can be produced by subjecting compound (33) to a reduction reaction. Compound (35) can be produced by subjecting compound (34) to a reduction reaction. Compound (36) can be produced by subjecting compound (35) to an azidation reaction. Compound (1-vii) can be produced by subjecting compound (36) to a reduction reaction.

In the thus-obtained compound (I), an intramolecular functional group can also be converted to an object functional group by combining chemical reactions known per se. Examples of the chemical reaction include oxidation reaction, reduction reaction, alkylation reaction, acylation reaction, ureation reaction, hydrolysis reaction, amination reaction, esterification reaction, aryl coupling reaction, deprotection reaction and the like.

Compound (I) obtained by the above-mentioned production method can be isolated and purified by a known means, such as solvent extraction, pH change of solution, phase transfer, crystallization, recrystallization, chromatography and the like.

When compound (I) has an optical isomer, a stereoisomer, a regioisomer or a rotamer, these are also encompassed in compound (I), and can be obtained as a single product according to synthesis and separation methods known per se. For example, when compound (I) contains an optical isomer, an optical isomer resolved from this compound is also encompassed in compound (I).

The optical isomer can be produced according to a method known per se.

Compound (I) may be a crystal.

A crystal of compound (I) (hereinafter sometimes to be abbreviated as the crystal of the present invention) can be produced by crystallization, by applying a crystallization method known per se.

The crystal of the present invention is superior in the physicochemical properties (e.g., melting point, solubility, stability) and biological properties (e.g., pharmacokinetics (absorbability, distribution, metabolism, excretion), efficacy), and is expected to be useful as a medicament.

EXAMPLE

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

Unless particularly indicated, the elution in column chromatography in the Examples was performed under observation by TLC (Thin Layer Chromatography). For TLC observation, 60 $F_{254}$ manufactured by Merck was used as a TLC plate, and the solvent used as an elution solvent for column chromatography was also used as developing solvent. For detection, moreover, a UV detector was adopted. In silica gel column chromatography, the indication of NH means use of aminopropylsilane-bonded silica gel, Diol means use of 3-(2,3-dihydroxypropoxy)propylsilane-bonded silica gel. In preparative HPLC (high performance liquid chromatography), the indication of C18 means use of octadecyl-bonded silica gel. The ratio shown for elution solvents is, unless otherwise specified, a volume mixing ratio.

For the analysis of $^1$H NMR, ACD/SpecManager (trade name) software and the like were used. Very mild peaks for protons of a hydroxy group, an amino group and the like are sometimes not described.

MS was measured by LC/MS. As ionization method, ESI method, or APCI method was used. The data indicates those found. Generally, molecular ion peaks are observed; however, they may be observed as a fragment ion. In the case of a salt, generally, a molecular ion peak or a fragment ion peak of a free form is observed.

The unit of sample concentration (c) in optical rotation ($[\alpha]_D$) is g/100 mL.

The elemental analytical value (Anal.) shows Calculated value (Calcd) and Found value (Found).

The peak in the powder X-ray diffraction in the Examples means a peak measured by Ultima IV (Rigaku Corporation, Japan) at room temperature using Cu Kα radiation as a radiation source. The measurement conditions were as follows.

Electric pressure/Electric current: 40 kV/50 mA
Scan speed: 6 degree/min
Scan range of 2 Theta: 2-35 degree The crystallinity by powder X-ray diffraction in the Examples was calculated by the Hermans method.

In the following Examples, the following abbreviations are used.
mp: melting point
MS: mass spectrum
M: mol concentration
N: normality
CDCl$_3$: deuterochloroform
DMSO-d$_6$: deuterodimethyl sulfoxide
$^1$H NMR: proton nuclear magnetic resonance
LC/MS: liquid chromatograph mass spectrometer
ESI: electrospray ionization
APCI: atmospheric pressure chemical ionization
HATU: O-(7-azabenzotriazol-1-yl)-N,N,N',N'-tetramethyl uronium hexafluorophosphate
DPPA: diphenylphosphoryl azide
TFA: trifluoroacetic acid
DIPEA: N-ethyl-N-isopropylpropane-2-amine
DMA: N,N-dimethylacetamide
DMF: N,N-dimethylformamide
HOBt: 1H-benzotriazol-1-ol
HOBt·H$_2$O: 1H-benzotriazol-1-ol hydrate
THF: tetrahydrofuran
WSC·HCl: N-(3-(dimethylamino)propyl)-N'-ethylcarbodiimide hydrochloride
Boc$_2$O: di-tert-butyl dicarbonate
DBU: 2,3,4,6,7,8,9,10-octahydropyrimido[1,2-a]azepine
TEA: triethylamine
Pd(PPh$_3$)$_4$: tetrakis(triphenylphosphine)palladium(0)

Example 5

6-(difluoromethoxy)-5-fluoro-N-[(4-methoxypyridin-3-yl)methyl]pyridine-3-carboxamide A mixture of 1-(4-methoxypyridin-3-yl)methanamine (1.00 g), 6-(difluoromethoxy)-5-fluoropyridine-3-carboxylic acid (1.499 g), WSC(HCl) (2.081 g), HOBt (1.174 g), triethylamine (3.03 ml) and DMF (20 ml) was stirred at room temperature overnight. Water was added to the mixture, and the precipitated solid was collected by filtration. The solid was recrystallized from ethyl acetate/hexane to give the title compound (1.870 g).

$^1$H NMR (300 MHz, DMSO-d$_6$) δ3.89 (3H, s), 4.46 (2H, d, J=5.7 Hz), 7.06 (1H, d, J=5.7 Hz), 7.51-8.07 (1H, m), 8.27-8.36 (2H, m), 8.39 (1H, d, J=5.7 Hz), 8.58 (1H, d, J=1.9 Hz), 9.08 (1H, t, J=5.5 Hz).

Example 6

6-(difluoromethoxy)-5-fluoro-N-[(5-fluoro-4-methoxypyridin-3-yl)methyl]pyridine-3-carboxamide A) 5-fluoro-4-methoxypyridine-3-carbaldehyde To a solution of 4-chloro-5-fluoronicotinaldehyde (1.15 g) in methanol (20 ml) was added 28% sodium methoxide methanol solution (2.086 g) at 0° C., and the mixture was stirred at 50° C. for 3 hr. Water was added to the mixture, and the precipitated solid was collected by filtration to give the title compound (0.880 g).

MS: 156.1.

B) (5-fluoro-4-methoxypyridin-3-yl)methanol

A mixture of 5-fluoro-4-methoxypyridine-3-carbaldehyde (875 mg), ethanol (10 ml) and sodium tetrahydroborate (235 mg) was stirred at room temperature for 1 hr. To the reaction mixture was added saturated aqueous ammonium chloride solution at 0° C., and the mixture was concentrated under reduced pressure. The residue was purified by silica gel column chromatography (methanol/ethyl acetate) to give the title compound (800 mg).

MS: 158.1.

C) 3-(azidomethyl)-5-fluoro-4-methoxypyridine

To a mixture of (5-fluoro-4-methoxypyridin-3-yl)methanol (800 mg), DBU (1.611 ml) and THF (20 ml) was added DPPA (2.299 ml) at 0° C., and the mixture was stirred at room temperature overnight. The mixture was concentrated under reduced pressure, and the residue was purified by silica gel column chromatography (ethyl acetate/hexane) to give the title compound (927 mg).

MS: 183.1.

D) 1-(5-fluoro-4-methoxypyridin-3-yl)methanamine

A mixture of 3-(azidomethyl)-5-fluoro-4-methoxypyridine (910 mg), triphenylphosphine (1572 mg), THF (10 ml)

and water (2.5 ml) was stirred at room temperature overnight. The mixture was concentrated under reduced pressure, and the residue was purified by silica gel column chromatography (methanol/ethyl acetate) to give the title compound (506 mg).
MS: 157.1.

E) 6-(difluoromethoxy)-5-fluoro-N-[(5-fluoro-4-methoxypyridin-3-yl)methyl]pyridine-3-carboxamide A mixture of 1-(5-fluoro-4-methoxypyridin-3-yl)methanamine (500 mg), 6-(difluoromethoxy)-5-fluoropyridine-3-carboxylic acid (663 mg), WSC(HCl) (921 mg), HOBt (519 mg), triethylamine (1.339 ml) and DMF (10 ml) was stirred at room temperature overnight. Water was added to the mixture, and the precipitated solid was collected by filtration to give the title compound (820 mg).
$^1$H NMR (300 MHz, DMSO-$d_6$) δ4.09 (314, d, J=4.1 Hz), 4.49 (214, d, J=5.7 Hz), 7.52-8.07 (1H, m), 8.26-8.39 (2H, m), 8.46 (1H, d, J=4.1 Hz), 8.57 (1H, d, J=1.9 Hz), 9.16 (1H, t, J=5.5 Hz).

Example 12

6-(difluoromethoxy)-5-fluoro-N-[(4-methoxypyrimidin-5-yl)methyl]pyridine-3-carboxamide A) 4-chloro-6-methoxypyrimidine-5-carbaldehyde To a mixture of 4,6-dichloropyrimidine-5-carbaldehyde (10 g) and methanol (500 ml) was added sodium hydrogen carbonate (5.22 g), and the mixture was stirred at room temperature overnight. The mixture was concentrated under reduced pressure, and water was added to the residue, and the mixture was extracted with ethyl acetate. The organic layer was separated, washed with water and saturated brine, dried over anhydrous sodium sulfate, and concentrated under reduced pressure. The residue was purified by silica gel column chromatography (ethyl acetate/hexane) to give the title compound (5.20 g).
MS: [M+H]$^+$ 173.1.

B) 4-methoxypyrimidine-5-carbaldehyde

A mixture of 4-chloro-6-methoxypyrimidine-5-carbaldehyde (5.2 g), triethylamine (5.04 ml), 10% palladium carbon (50% wet) (0.5 g) and ethanol (200 ml) was stirred under a normal pressure hydrogen atmosphere at room temperature overnight. The catalyst was filtered off, and the filtrate was concentrated under reduced pressure. Water was added to the obtained residue, and the mixture was extracted with ethyl acetate. The organic layer was separated, washed with water and saturated brine, dried over anhydrous sodium sulfate, and concentrated under reduced pressure to give the title compound (3.1 g).
MS: [M+H]$^+$ 139.1.

C) (4-methoxypyrimidin-5-yl)methanol

To a mixture of 4-methoxypyrimidine-5-carbaldehyde (3.1 g) and methanol (100 ml) was added sodium borohydride (1.274 g) by small portions at room temperature, and the mixture was stirred at room temperature for 1 hr. Water was added to the mixture, and the mixture was concentrated under reduced pressure, and extracted with ethyl acetate. The organic layer was separated, washed with water and saturated brine, dried over anhydrous sodium sulfate, and concentrated under reduced pressure to give the title compound (2.46 g).
MS: [M+H]$^+$ 141.1.

D) 1-(4-methoxypyrimidin-5-yl)methanamine

To a solution of (4-methoxypyrimidin-5-yl)methanol (2.46 g) in toluene (100 ml) were added DPPA (5.67 ml) and DBU (5.29 ml), and the mixture was stirred at 60° C. for 1 hr. The mixture was concentrated under reduced pressure, and the residue was purified by silica gel column chromatography (ethyl acetate/hexane) to give 5-(azidomethyl)-4-methoxypyrimidine as a crude product. To a solution of the crude product (2.9 g) in THE (100 ml) and water (25 ml) was added triphenylphosphine (5.30 g), and the mixture was stirred at room temperature overnight. The mixture was concentrated under reduced pressure, and the residue was purified by silica gel column chromatography (NH, ethyl acetate/hexane, then ethyl acetate/methanol) to give the title compound (2.25 g).
MS: [M+H]$^+$ 140.1.

E) 6-(difluoromethoxy)-5-fluoro-N-[(4-methoxypyrimidin-5-yl)methyl]pyridine-3-carboxamide A mixture of 6-(difluoromethoxy)-5-fluoropyridine-3-carboxylic acid (1.47 g), 1-(4-methoxypyrimidin-5-yl)methanamine (1 g), WSC(HCl) (1.55 g), HOBt (1.10 g) and DMF (30 ml) was stirred at room temperature overnight. The mixture was concentrated under reduced pressure, water was added to the residue, and the mixture was extracted with ethyl acetate. The organic layer was separated, washed with water and brine, dried over anhydrous sodium sulfate, and concentrated under reduced pressure. The residue was purified by silica gel column chromatography (NH, ethyl acetate/hexane) and then by silica gel column chromatography (ethyl acetate/hexane). The obtained solid was crystallized from ethyl acetate/hexane to give the title compound (1.53 g).
$^1$H NMR (300 MHz, DMSO-$d_6$) δ 3.99 (3H, s), 4.42 (2H, d, J=5.3 Hz), 7.80 (1H, t, J=71.4 Hz), 8.31 (1H, dd, J=10.6, 1.9 Hz), 8.45 (1H, s), 8.57 (1H, d, J=1.9 Hz), 8.72 (1H, s), 9.14 (1H, br t, J=5.1 Hz).

Example 18

6-(difluoromethoxy)-5-fluoro-N-[(4-methylpyridin-3-yl)methyl]pyridine-3-carboxamide A) 1-(4-methylpyridin-3-yl)methanamine To a mixture of 4-methylnicotinonitrile (2.5 g), cobalt(II) chloride 6 hydrate (2.52 g) and methanol (80 ml) was added sodium borohydride (5.60 g) by small portions at 0° C., and the mixture was stirred at room temperature for 1 hr. Water was added to the mixture at 0° C., and ethyl acetate, 2N aqueous sodium hydroxide solution, and saturated brine were added. Insoluble material was filtered off, anhydrous sodium sulfate was added to the filtrate, and the insoluble material was filtered off again. Ethyl acetate and isopropanol were added to the filtrate. The organic layer was separated, washed with water and saturated brine, dried over anhydrous sodium sulfate, and concentrated under reduced pressure to give the title compound (820 mg).
MS: [M+H]$^+$ 123.2.

B) 6-(difluoromethoxy)-5-fluoro-N-[(4-methylpyridin-3-yl)methyl]pyridine-3-carboxamide To a mixture of 6-(difluoromethoxy)-5-fluoropyridine-3-carboxylic acid (1000 mg), 1-(4-methylpyridin-3-yl)methanamine (767 mg), HATU (2387 mg) and THF (12 ml) was added N,N-diisopropylethylamine (2.53 ml), and the mixture was stirred at room temperature for 2 hr. To the mixture was added saturated aqueous sodium hydrogen carbonate solution, and the mixture was extracted with ethyl acetate. The organic layer was separated, washed with water and saturated brine, dried over anhydrous sodium sulfate, and concentrated under reduced pressure. The residue was purified by silica gel column chromatography (NH, ethyl acetate/hexane). The obtained solid was crystallized from ethyl acetate/hexane to give the title compound (1050 mg).
$^1$H NMR (300 MHz, CDCl$_3$) δ2.39 (3H, s), 4.68 (2H, d, J=5.3 Hz), 6.50 (1H, brs), 7.14 (1H, d, J=5.3 Hz), 7.49 (1H, t, J=72.9 Hz), 7.99 (1H, dd, J=9.4, 1.9 Hz), 8.37 (1H, d, J=1.9 Hz), 8.39-8.43 (2H, m).

Example 19

N-{[4-(cyclopropyloxy)pyrimidin-5-yl]methyl}-6-(difluoromethoxy)-5-fluoropyridine-3-carboxamide A) Ethyl 4-hydroxypyrimidine-5-carboxylate To a mixture of formamidine hydrochloride (1:1) (31.4 g), diethyl (2-ethoxymethylene)malonate (78 ml) and ethanol (200 ml) was added dropwise 20% sodium ethoxide ethanol solution (133 g) at 0° C. The mixture was stirred at 0° C. for 3 hr, and 20% sodium ethoxide ethanol solution (133 g) was added. The mixture was stirred at room temperature for 16 hr. The mixture was concentrated under reduced pressure, and water was added to the residue. The obtained aqueous solution was washed with diethyl ether, and the aqueous layer was acidified (pH=3) with 1N hydrochloric acid and stirred at room temperature for 1 hr. The precipitated solid was collected by filtration, and washed with diethyl ether to give the title compound (48.74 g).
MS: [M+H]$^+$ 169.1.

B) Ethyl 4-chloropyrimidine-5-carboxylate

To phosphoric trichloride (56.5 ml) was added ethyl 4-hydroxypyrimidine-5-carboxylate (10 g) by small portions at room temperature, and the mixture was stirred at 110° C. for 2 hr. The mixture was concentrated under reduced pressure, toluene was added to the residue, and the mixture was concentrated under reduced pressure. To the obtained residue were added ethyl acetate and water at 0° C., and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (5.78 g).
MS: [M+H]$^+$ 187.1.

C) Ethyl 4-(cyclopropyloxy)pyrimidine-5-carboxylate

To a mixture of ethyl 4-chloropyrimidine-5-carboxylate (3.50 g), cyclopropanol (1.198 g) and THF (70 ml) was added dropwise a mixture of potassium tert-butoxide (2.53 g) and THF (35 m 1) under a nitrogen atmosphere at 0° C. The mixture was stirred under a nitrogen atmosphere at 0° C. for 1 hr. The mixture was concentrated under reduced pressure, water was added to the residue, and the mixture was extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (3.082 g).
MS: [M+H]$^+$ 209.2.

D) [4-(cyclopropyloxy)pyrimidin-5-yl]methanol

To a mixture of lithium aluminum hydride (182 mg) and THF (15 ml) was added dropwise a mixture of ethyl 4-(cyclopropyloxy)pyrimidine-5-carboxylate (500 mg) and THF (10 ml) under a nitrogen atmosphere at −40° C. The mixture was stirred under a nitrogen atmosphere at −40° C. for 1 hr, and sodium sulfate 10 hydrate (1.547 g) was added. The mixture was stirred at −40° C. for 30 min, and at room temperature overnight. To a mixture of lithium aluminum hydride (547 mg) and 11-IF (30 ml) was added dropwise a mixture of ethyl 4-(cyclopropyloxy)pyrimidine-5-carboxylate (1.00 g) and THF (20 ml) under a nitrogen atmosphere at −40° C. The mixture was stirred under a nitrogen atmosphere at −40° C. for 1 hr, and sodium sulfate 10 hydrate (4.64 g) was added. The mixture was stirred at −40° C. for 30 min, and at room temperature overnight. The obtained two mixtures were combined, insoluble material was filtered off, and the filtrate was evaporated under reduced pressure. The residue was purified by silica gel column chromatography (ethyl acetate/hexane) to give the title compound (627 mg).
MS: [M+H]$^+$ 167.2.

E) 5-(azidomethyl)-4-(cyclopropyloxy)pyrimidine

A mixture of [4-(cyclopropyloxy)pyrimidin-5-yl]methanol (700 mg), DPPA (1391 mg), DBU (962 mg) and toluene (70 ml) was stirred at 60° C. for 1 hr. Water was added to the mixture, and the mixture was extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (694 mg).
MS: [M+H]$^+$ 192.2.

F) 1-[4-(cyclopropyloxy)pyrimidin-5-yl]methanamine

A mixture of 5-(azidomethyl)-4-(cyclopropyloxy)pyrimidine (690 mg), triphenylphosphine (1420 mg), THF (20 ml) and water (5 ml) was stirred at 60° C. for 2 hr. The mixture was concentrated under reduced pressure, and the residue was purified by silica gel column chromatography (NH, ethyl acetate/hexane, then ethyl acetate/methanol) to give the title compound (578 mg).
MS: [M+H]$^+$ 166.3.

G) N-{[4-(cyclopropyloxy)pyrimidin-5-yl]methyl}-6-(di fluoromethoxy)-5-fluoropyridine-3-carboxamide To a mixture of 1-[4-(cyclopropyloxy)pyrimidin-5-yl]methanamine (550 mg) and acetonitrile (20 ml) were added 6-(difluoromethoxy)-5-fluoropyridine-3-carboxylic acid (690 mg), HATU (1519 mg) and N,N-diisopropylethylamine (0.872 ml), and the mixture was stirred at room temperature for 1 hr. The mixture was concentrated under reduced pressure, saturated aqueous sodium hydrogen carbonate solution was added to the residue, and the mixture was extracted with ethyl acetate. The organic layer was washed with saturated brine, dried over anhydrous magnesium sulfate, and concentrated under reduced pressure. The residue was purified by silica gel column chromatography (NH, ethyl acetate/hexane). The obtained solid was recrystallized from ethyl acetate/hexane to give the title compound (943 mg).

$^1$H NMR (300 MHz, DMSO-$d_6$) δ 0.65-0.89 (4H, m), 4.36 (2H, d, J=5.3 Hz), 4.39-4.47 (1H, m), 7.80 (1H, t, J=71.6 Hz), 8.29 (1H, dd, J=10.6, 1.9 Hz), 8.47 (1H, s), 8.55 (1H, d, J=1.9 Hz), 8.75 (1H, s), 9.06 (1H, t, J=5.5 Hz).

Example 21

5-chloro-6-(difluoromethoxy)-N-[(4-methoxypyrimidin-5-yl)methyl]pyridine-3-carboxamide A mixture of 5-chloro-6-(difluoromethoxy)pyridine-3-carboxylic acid (169 mg), 1-(4-methoxypyrimidin-5-yl)methanamine (100 mg), WSC(HCl) (165 mg), HOBt (117 mg) and DMF (8 ml) was stirred at room temperature overnight. The mixture was concentrated under reduced pressure, and the residue was purified by silica gel column chromatography (NH, ethyl acetate/hexane), and then by silica gel column chromatography (ethyl acetate/hexane). The obtained residue was crystallized from ethyl acetate/hexane to give the title compound (109 mg).

$^1$H NMR (300 MHz, DMSO-$d_6$) δ 3.99 (3H, s), 4.42 (2H, d, J=5.3 Hz), 7.52-8.08 (1H, m), 8.46 (1H, s), 8.52 (1H, d, J=1.9 Hz), 8.67 (1H, d, J=1.9 Hz), 8.72 (1H, s), 9.14 (1H, t, J=5.3 Hz).

Example 22

3-fluoro-N-[(4-methoxypyrimidin-5-yl)methyl]-4-(trifluoromethoxy)benzamide

A mixture of 3-fluoro-4-(trifluoromethoxy)benzoic acid (322 mg), 1-(4-methoxypyrimidin-5-yl)methanamine (200 mg), WSC(HCl) (276 mg), HOBt (194 mg) and DMF (15 ml) was stirred at room temperature overnight. The mixture was concentrated under reduced pressure, and the residue was purified by silica gel column chromatography (NH, ethyl acetate/hexane). The obtained residue was crystallized from ethyl acetate/hexane to give the title compound (355 mg).

$^1$H NMR (300 MHz, DMSO-$d_6$) δ 3.99 (3H, s), 4.41 (2H, d, J=5.7 Hz), 7.71 (1H, td, J=8.1, 1.1 Hz), 7.81-7.89 (1H, m), 7.98 (1H, dd, J=11.3, 1.9 Hz), 8.43 (1H, s), 8.72 (1H, s), 9.10 (1H, t, J=5.3 Hz).

Example 24

6-(difluoromethoxy)-N-[(4-ethoxypyrimidin-5-yl)methyl]-5-fluoropyridine-3-carboxamide B) (4-ethoxypyrimidin-5-yl)methanol To a solution of ethyl 4-ethoxypyrimidine-5-carboxylate (1.06 g) in THF (50 ml) was added lithium aluminum hydride (0.205 g) under a nitrogen atmosphere at −40° C. The reaction mixture was stirred under a nitrogen atmosphere at −40° C. for 1 hr, and sodium sulfate 10 hydrate (1.741 g) was added. The mixture was stirred at −40° C. for 30 min, then at room temperature for 1 hr. Insoluble material was filtered off, and the filtrate was concentrated under reduced pressure. The residue was purified by silica gel column chromatography (ethyl acetate/hexane) to give the title compound (440 mg).

MS: [M+H]$^+$ 155.2.

C) 5-(azidomethyl)-4-ethoxypyrimidine

A mixture of (4-ethoxypyrimidin-5-yl)methanol (440 mg), DBU (0.860 ml), DPPA (0.920 ml) and toluene (30 ml) was stirred at 60° C. for 2 hr. The mixture was concentrated under reduced pressure, and the residue was purified by silica gel column chromatography (ethyl acetate/hexane) to give the title compound (470 mg).

MS: [M+H]$^+$ 180.2.

D) 1-(4-ethoxypyrimidin-5-yl)methanamine

A mixture of 5-(azidomethyl)-4-ethoxypyrimidine (470 mg), triphenylphosphine (1376 mg), water (4 ml) and THF (20 ml) was stirred at room temperature for 16 hr. The mixture was concentrated under reduced pressure, and the residue was purified by silica gel column chromatography (ethyl acetate/hexane, then ethyl acetate/methanol) to give the title compound (390 mg).

MS: [M+H]$^+$ 154.2.

E) 6-(difluoromethoxy)-N-[(4-ethoxypyrimidin-5-yl)methyl]-5-fluoropyridine-3-carboxamide A mixture of 1-(4-ethoxypyrimidin-5-yl)methanamine (180 mg), HATU (536 mg), N,N-diisopropylethylamine (0.821 ml), 6-(difluoromethoxy)-5-fluoropyridine-3-carboxylic acid (243 mg) and DMF (5 ml) was stirred at room temperature for 1 hr. Water was added to the mixture, and the mixture was extracted with ethyl acetate. The organic layer was washed with water and brine, dried over anhydrous magnesium sulfate, and concentrated under reduced pressure. The residue was purified by silica gel column chromatography (ethyl 0.10 acetate/hexane), and then by silica gel column chromatography (NH, ethyl acetate/hexane). The obtained solid was washed with hexane, and recrystallized from ethyl acetate/hexane to give the title compound (270 mg).

$^1$H NMR (300 MHz, DMSO-$d_6$) δ 1.34 (3H, t, J=7.2 Hz), 4.35-4.53 (4H, m), 7.80 (1H, t, J=71.6 Hz), 8.31 (1H, dd, J=10.6, 1.9 Hz), 8.44 (1H, s), 8.57 (1H, d, J=1.9 Hz), 8.69 (1H, s), 9.11 (1H, t, J=5.5 Hz).

Example 40

6-(difluoromethoxy)-5-fluoro-N-[(5-fluoro-4-methylpyridin-3-yl)methyl]pyridine-3-carboxamide A) 5-fluoro-4-methylpyridine-3-carbonitrile A mixture of copper(I) cyanide (3.11 g), 3-bromo-5-fluoro-4-methylpyridine (3.3 g) and DMF (100 ml) was stirred at 140° C. for 20 hr. The mixture was concentrated under reduced pressure to an about half amount. To the mixture were added 20% aqueous ammonia and water, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (1.26 g).

MS: [M+H]$^+$ 137.2.

B) 1-(5-fluoro-4-methylpyridin-3-yl)methanamine

A mixture of Raney (registered trade mark) cobalt (OFT MS, Kawaken Fine Chemicals Co., Ltd.) (567 mg), 5-fluoro-4-methylpyridine-3-carbonitrile (1.26 g) and 7 M ammonia methanol solution (30 ml) was stirred under 5 MPa hydrogen atmosphere at 70° C. for 3 hr. The catalyst was filtered off, and the filtrate was concentrated under reduced pressure to give the title compound (1.26 g).

MS: [M+H]$^+$ 141.1.

C) 6-(difluoromethoxy)-5-fluoro-N-[(5-fluoro-4-methylpyridin-3-yl)methyl]pyridine-3-carboxamide A mixture of 1-(5-fluoro-4-methylpyridin-3-yl)methanamine (600 mg), HATU (1953 mg), N,N-diisopropylethylamine (1.495 ml), 6-(difluoromethoxy)-5-fluoropyridine-3-carboxylic acid (887 mg) and DMF (10 ml) was stirred at room temperature for 16 hr. Water was added to the mixture, and the mixture was extracted with ethyl acetate. The organic layer was separated, washed with water and saturated brine, dried over anhydrous magnesium sulfate, and concentrated under reduced pressure. The residue was purified by silica gel column chromatography (NH, ethyl acetate/hexane). The obtained solid was washed with hexane and crystallized from ethyl acetate/hexane to give the title compound (590 mg).

$^1$H NMR (300 MHz, DMSO-d$_6$) δ 2.29 (3H, d, J=1.5 Hz), 4.55 (2H, d, J=5.3 Hz), 7.80 (1H, t, J=71.6 Hz), 8.28-8.34 (1H, m), 8.36 (1H, s), 8.41 (1H, s), 8.57 (1H, d, J=1.9 Hz), 9.17 (1H, br t, J=5.3 Hz).

The Example compounds are shown in the following Tables. In the Tables, MS shows measured values. The compounds of Examples 1-124 in the following Tables were produced according to the methods shown in the above-mentioned Examples or methods analogous thereto.

TABLE 1-1

| Ex. No. | IUPAC name | structural formula | salt | MS |
|---|---|---|---|---|
| 1 | N-[(5-methoxypyridin-3-yl)methyl]-4-(trifluoromethoxy)benzamide | | free base/acid | |
| 2 | N-[(5-chloropyridin-3-yl)methyl]-4-(trifluoromethoxy)benzamide | | free base/acid | |
| 3 | N-[(5-bromopyridin-3-yl)methyl]-4-(trifluoromethoxy)benzamide | | free base/acid | |
| 4 | N-[(4-methylpyridin-3-yl)methyl]-4-(trifluoromethoxy)benzamide | | free base/acid | 310.9 |
| 5 | 6-(difluoromethoxy)-5-fluoro-N-[(4-methoxypyridin-3-yl)methyl]pyridine-3-carboxamide | | free base/acid | 328.1 |

TABLE 1-1-continued

| Ex. No. | IUPAC name | structural formula | salt | MS |
|---|---|---|---|---|
| 6 | 6-(difluoromethoxy)-5-fluoro-N-[(5-fluoro-4-methoxypyridin-3-yl)methyl]pyridine-3-carboxamide | | free base/acid | 346.1 |
| 7 | N-[(4-methoxypyridin-3-yl)methyl]-4-(trifluoromethoxy)benzamide | | free base/acid | 327.1 |
| 8 | 3-fluoro-N-[(4-methoxypyridin-3-yl)methyl]-4-(trifluoromethoxy)-benzamide | | free base/acid | 345.0 |

TABLE 1-2

| Ex. No. | IUPAC name | structural formula | salt | MS |
|---|---|---|---|---|
| 9 | 3-fluoro-N-[(4-methoxypyridin-3-yl)methyl]-4-(trifluoromethyl)benzamide | | free base/acid | 329.1 |
| 10 | 6-(difluoromethoxy)-N-[(4-ethoxypyridin-3-yl)methyl]-5-fluoropyridine-3-carboxamide | | free base/acid | 342.1 |
| 11 | 4-(difluoromethoxy)-N-[(4-ethoxypyridin-3-yl)methyl]-3-fluorobenzamide | | free base/acid | 341.1 |

TABLE 1-2-continued

| Ex. No. | IUPAC name | structural formula | salt | MS |
|---|---|---|---|---|
| 12 | 6-(difluoromethoxy)-5-fluoro-N-[(4-methoxypyrimidin-5-yl)methyl]pyridine-3-carboxamide | | free base/acid | 329.1 |
| 13 | 4-(difluoromethoxy)-3-fluoro-N-[(4-methoxypyrimidin-5-yl)methyl]benzamide | | free base/acid | 328.1 |
| 14 | N-{[4-(cyclopropyloxy)pyridin-3-yl]methyl}-6-(difluoromethoxy)-5-fluoropyridine-3-carboxamide | | free base/acid | 354.1 |
| 15 | N-[(4-cyclopropylpyridin-3-yl)methyl]-6-(difluoromethoxy)-5-fluoropyridine-3-carboxamide | | free base/acid | 338.1 |
| 16 | 6-(difluoromethoxy)-5-fluoro-N-{[4-(trifluoromethyl)pyridin-3-yl]methyl}pyridine-3-carboxamide | | free base/acid | 364.1 |

TABLE 1-3

| Ex. No. | IUPAC name | structural formula | salt | MS |
|---|---|---|---|---|
| 17 | 5-chloro-6-(difluoromethoxy)-N-[(4-methoxypyridin-3-yl)methyl]pyridine-3-carboxamide | | free base/acid | 344.1 |
| 18 | 6-(difluoromethoxy)-5-fluoro-N-[(4-methylpyridin-3-yl)methyl]pyridine-3-carboxamide | | free base/acid | 312.1 |

TABLE 1-3-continued

| Ex. No. | IUPAC name | structural formula | salt | MS |
|---|---|---|---|---|
| 19 | N-{[4-(cyclopropyloxy)pyrimidin-5-yl]methyl}-6-(difluoromethoxy)-5-fluoropyridine-3-carboxamide | | free base/acid | 355.1 |
| 20 | 6-(difluoromethoxy)-5-fluoro-N-({4-[(propan-2-yl)oxy]pyrimidin-5-yl}methyl)pyridine-3-carboxamide | | free base/acid | 357.0 |
| 21 | 5-chloro-6-(difluoromethoxy)-N-[(4-methoxypyrimidin-5-yl)methyl]pyridine-3-carboxamide | | free base/acid | 345.0 |
| 22 | 3-fluoro-N-[(4-methoxypyrimidin-5-yl)methyl]-4-(trifluoromethoxy)benzamide | | free base/acid | 346.1 |
| 23 | N-[(4-cyclopropylpyrimidin-5-yl)methyl]-6-(difluoromethoxy)-5-fluoropyridine-3-carboxamide | | free base/acid | 339.1 |
| 24 | 6-(difluoromethoxy)-N-[(4-ethoxypyrimidin-5-yl)methyl]-5-fluoropyridine-3-carboxamide | | free base/acid | 343.1 |

TABLE 1-4

| Ex. No. | IUPAC name | structural formula | salt | MS |
|---|---|---|---|---|
| 25 | 4-(difluoromethoxy)-N-[(4-methoxypyrimidin-5-yl)methyl]benzamide | | free base/acid | 309.9 |

TABLE 1-4-continued

| Ex. No. | IUPAC name | structural formula | salt | MS |
|---|---|---|---|---|
| 26 | N-[(4-methoxypyrimidin-5-yl)methyl]-4-(trifluoromethoxy)-benzamide | | free base/acid | 327.9 |
| 27 | 5-chloro-6-(difluoromethoxy)-N-[(4-methylpyridin-3-yl)methyl]pyridine-3-carboxamide | | free base/acid | 327.9 |
| 28 | 6-(difluoromethoxy)-N-[(4-ethylpyrimidin-5-yl)methyl]-5-fluoropyridine-3-carboxamide | | free base/acid | 327.0 |
| 29 | N-{[4-(1,1-difluoroethyl)-pyrimidin-5-yl]methyl}-6-(difluoromethoxy)-5-fluoropyridine-3-carboxamide | | free base/acid | 363.0 |
| 30 | 3-fluoro-N-[(4-methylpyrimidin-5-yl)methyl]-4-(trifluoromethoxy)-benzamide | | free base/acid | 329.9 |
| 31 | 6-(difluoromethoxy)-5-fluoro-N-[(4-methylpyrimidin-5-yl)methyl]pyridine-3-carboxamide | | free base/acid | 312.9 |
| 32 | N-({4-[(3,3-difluorocyclobutyl)-oxy]pyrimidin-5-yl}methyl)-6-(difluoromethoxy)-5-fluoropyridine-3-carboxamide | | free base/acid | 405.0 |

TABLE 1-5

| Ex. No. | IUPAC name | structural formula | salt | MS |
|---|---|---|---|---|
| 33 | 5-fluoro-N-[(4-methoxypyrimidin-5-yl)methyl]-6-(trifluoromethoxy)pyridine-3-carboxamide | | free base/acid | 347.0 |
| 34 | 5-fluoro-N-[(4-methoxypyridin-3-yl)methyl]-6-(trifluoromethoxy)pyridine-3-carboxamide | | free base/acid | 346.1 |
| 35 | 5-fluoro-N-[(4-methylpyridin-3-yl)methyl]-6-(trifluoromethoxy)-pyridine-3-carboxamide | | free base/acid | 330.1 |
| 36 | N-{[4-(3,3-difluorocyclobutyl)-pyrimidin-5-yl]methyl}-6-(difluoromethoxy)-5-fluoropyridine-3-carboxamide | | free base/acid | 387.1 |
| 37 | N-{[4-(2,2-difluorocyclopropyl)-pyrimidin-5-yl]methyl}-6-(difluoromethoxy)-5-fluoropyridine-3-carboxamide | | free base/acid | 373.1 |
| 38 | 6-(difluoromethoxy)-N-[(4-ethylpyridin-3-yl)methyl]-5-fluoropyridine-3-carboxamide | | free base/acid | 325.9 |
| 39 | N-{[4-(cyclopropyloxy)-5-fluoropyridin-3-yl]methyl}-6-(difluoromethoxy)-5-fluoropyridine-3-carboxamide | | free base/acid | 371.9 |

TABLE 1-5-continued

| Ex. No. | IUPAC name | structural formula | salt | MS |
|---|---|---|---|---|
| 40 | 6-(difluoromethoxy)-5-fluoro-N-[(5-fluoro-4-methylpyridin-3-yl)methyl]pyridine-3-carboxamide | | free base/acid | 327.9 |

TABLE 1-6

| Ex. No. | IUPAC name | structural formula | salt | MS |
|---|---|---|---|---|
| 41 | 6-(difluoromethoxy)-N-[(4-ethyl-5-fluoropyridin-3-yl)methyl]-5-fluoropyridine-3-carboxamide | | free base/acid | 341.9 |
| 42 | 6-(difluoromethoxy)-5-fluoro-N-[(5-methoxypyridin-3-yl)methyl]pyridine-3-carboxamide | | free base/acid | 327.9 |
| 43 | N-{[4-(1,1-difluoroethyl)pyridin-3-yl]methyl}-6-(difluoromethoxy)-5-fluoropyridine-3-carboxamide | | free base/acid | 359.9 |
| 44 | 5-fluoro-6-methoxy-N-[(4-methylpyridin-3-yl)methyl]pyridine-3-carboxamide | | free base/acid | 276.0 |
| 45 | 6-ethoxy-5-fluoro-N-[(4-methylpyridin-3-yl)methyl]pyridine-3-carboxamide | | free base/acid | 289.9 |
| 46 | 6-cyclopropyl-5-fluoro-N-[(4-methylpyridin-3-yl)methyl]pyridine-3-carboxamide | | free base/acid | 286.0 |
| 47 | N-[(5-chloro-4-methylpyridin-3-yl)methyl]-6-(difluoromethoxy)-5-fluoropyridine-3-carboxamide | | free base/acid | 343.9 |

TABLE 1-6-continued

| Ex. No. | IUPAC name | structural formula | salt | MS |
|---|---|---|---|---|
| 48 | 4-(difluoromethoxy)-3-fluoro-N-[(4-methylpyridin-3-yl)methyl]benzamide | 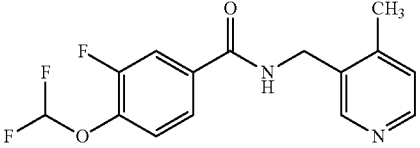 [SMILES: Cc1ccncc1CNC(=O)c1cnc(OC(F)F)c(F)c1] | free base/acid | 311.1 |

TABLE 1-7

| Ex. No. | IUPAC name | structural formula | salt | MS |
|---|---|---|---|---|
| 49 | 3-fluoro-N-[(4-methylpyridin-3-yl)methyl]-4-(trifluoromethoxy)benzamide | 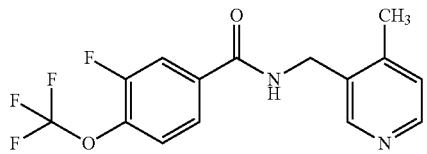 [SMILES: Cc1ccncc1CNC(=O)c1ccc(OC(F)(F)F)c(F)c1] | free base/acid | 329.1 |
| 50 | 4-(difluoromethoxy)-N-[(4-methylpyridin-3-yl)methyl]benzamide | 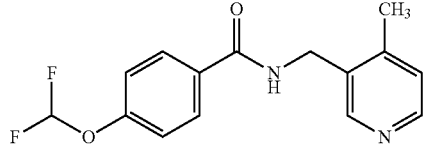 [SMILES: Cc1ccncc1CNC(=O)c1ccc(OC(F)F)cc1] | free base/acid | 293.1 |
| 51 | 6-(difluoromethoxy)-N-[(4-methylpyridin-3-yl)methyl]pyridine-3-carboxamide | 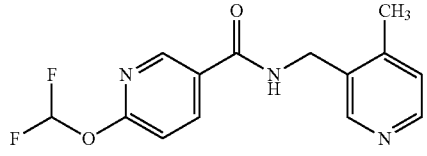 [SMILES: Cc1ccncc1CNC(=O)c1ccc(OC(F)F)nc1] | free base/acid | 294.1 |
| 52 | 5-chloro-N-[(4-methylpyridin-3-yl)methyl]-6-(trifluoromethyl)pyridine-3-carboxamide | 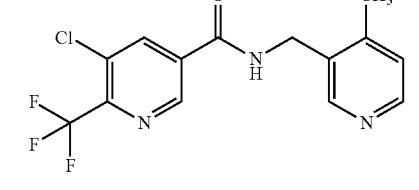 | free base/acid | 330.0 |
| 53 | 3-fluoro-N-[(4-methylpyridin-3-yl)methyl]-4-(trifluoromethyl)benzamide | 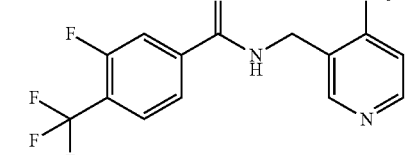 | free base/acid | 313.1 |
| 54 | 3-chloro-N-[(4-methylpyridin-3-yl)methyl]-4-(trifluoromethyl)benzamide | 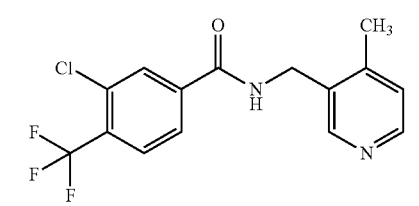 [SMILES: Cc1ccncc1CNC(=O)c1ccc(C(F)(F)F)c(Cl)c1] | free base/acid | 329.1 |

TABLE 1-7-continued

| Ex. No. | IUPAC name | structural formula | salt | MS |
|---|---|---|---|---|
| 55 | 4-(difluoromethoxy)-3,5-difluoro-N-[(4-methylpyridin-3-yl)methyl]benzamide | | free base/ acid | 329.1 |
| 56 | 5-cyclopropyl-N-[(4-methylpyridin-3-yl)methyl]thiophene-3-carboxamide | | free base/ acid | 273.1 |

TABLE 1-8

| Ex. No. | IUPAC name | structural formula | salt | MS |
|---|---|---|---|---|
| 57 | 4-(difluoromethyl)-3,5-difluoro-N-[(4-methylpyridin-3-yl)methyl]benzamide | | free base/ acid | 313.1 |
| 58 | 4-(difluoromethyl)-3-fluoro-N-[(4-methylpyridin-3-yl)methyl]benzamide | | free base/ acid | 295.1 |
| 59 | 3-chloro-4-(difluoromethyl)-N-[(4-methylpyridin-3-yl)methyl]benzamide | | free base/ acid | 311.0 |
| 60 | 3-fluoro-4-methoxy-N-[(4-methylpyridin-3-yl)methyl]benzamide | | free base/ acid | 275.1 |
| 61 | 6-(difluoromethoxy)-N-[(4-ethoxy-5-fluoropyridin-3-yl)methyl]-5-fluoropyridine-3-carboxamide | | free base/ acid | 360.1 |

TABLE 1-8-continued

| Ex. No. | IUPAC name | structural formula | salt | MS |
|---|---|---|---|---|
| 62 | 3,5-difluoro-4-methoxy-N-[(4-methoxypyrimidin-5-yl)methyl]benzamide | | free base/ acid | 310.1 |
| 63 | 4-(difluoromethoxy)-3,5-difluoro-N-[(4-methoxypyrimidin-5-yl)methyl]benzamide | | free base/ acid | 346.1 |
| 64 | N-[(4-methylpyridin-3-yl)methyl]-5-(trifluoromethyl)thiophene-2-carboxamide | | free base/ acid | 301.1 |

TABLE 1-9

| Ex. No. | IUPAC name | structural formula | salt | MS |
|---|---|---|---|---|
| 65 | 5-chloro-6-ethoxy-N-[(4-methylpyridin-3-yl)methyl]pyridine-3-carboxamide | | free base/ acid | 306.1 |
| 66 | 5-chloro-6-methoxy-N-[(4-methylpyridin-3-yl)methyl]pyridine-3-carboxamide | | free base/ acid | 292.1 |
| 67 | 3,5-difluoro-N-[(5-fluoro-4-methylpyridin-3-yl)methyl]-4-methoxybenzamide | | free base/ acid | 311.1 |
| 68 | 4-(difluoromethoxy)-3,5-difluoro-N-[(5-fluoro-4-methylpyridin-3-yl)methyl]benzamide | | free base/ acid | 347.1 |

TABLE 1-9-continued

| Ex. No. | IUPAC name | structural formula | salt | MS |
|---|---|---|---|---|
| 69 | 4-(difluoromethoxy)-3-fluoro-N-[(5-fluoro-4-methylpyridin-3-yl)methyl]benzamide | | free base/acid | 329.1 |
| 70 | 6-(difluoromethoxy)-N-{[4-(difluoromethyl)pyridin-3-yl]methyl)-5-fluoropyridine-3-carboxamide | | free base/acid | 348.0 |
| 71 | 3,5-difluoro-4-methoxy-N-[(4-methylpyridin-3-yl)methyl]benzamide | | free base/acid | 293.1 |
| 72 | 4-ethoxy-3,5-difluoro-N-[(4-methylpyridin-3-yl)methyl]benzamide | | free base/acid | 307.1 |

TABLE 1-10

| Ex. No. | IUPAC name | structural formula | salt | MS |
|---|---|---|---|---|
| 73 | 5-chloro-6-(difluoromethoxy)-N-[(5-fluoro-4-methylpyridin-3-yl)methyl]pyridine-3-carboxamide | | free base/acid | 346.0 |
| 74 | N-{[4-(cyclopropyloxy)-pyrimidin-5-yl]methyl}-3,5-difluoro-4-methoxybenzamide | | free base/acid | 336.1 |

TABLE 1-10-continued

| Ex. No. | IUPAC name | structural formula | salt | MS |
|---|---|---|---|---|
| 75 | N-{[4-(cyclopropyloxy)-pyrimidin-5-yl]methyl}-6-ethoxy-5-fluoropyridine-3-carboxamide | | free base/ acid | 333.1 |
| 76 | N-{[4-(cyclopropyloxy)-pyrimidin-5-yl]methyl}-4-(difluoromethoxy)-3,5-difluorobenzamide | | free base/ acid | 372.2 |
| 77 | N-{[4-(cyclopropyloxy)-pyrimidin-5-yl]methyl}-4-(difluoromethoxy)-3-fluorobenzamide | | free base/ acid | 354.1 |
| 78 | 5-chloro-N-{[4-(cyclopropyloxy)pyrimidin-5-yl]methyl}-6-(difluoromethoxy)pyridine-3-carboxamide | | free base/ acid | 371.1 |
| 79 | 5-cyclopropyl-N-[(4-methoxypyrimidin-5-yl)methyl]thiophene-3-carboxamide | | free base/ acid | 290.1 |
| 80 | 6-cyclopropyl-5-fluoro-N-[(5-fluoro-4-methylpyridin-3-yl)methyl]pyridine-3-carboxamide | | free base/ acid | |

TABLE 1-11

| Ex. No. | IUPAC name | structural formula | salt | MS |
|---|---|---|---|---|
| 81 | 6-cyclopropyl-N-{[4-(cyclopropyloxy)-pyrimidin-5-yl]methyl}-5-fluoropyridine-3-carboxamide | | free base/ acid | |
| 82 | 6-cyclopropyl-5-fluoro-N-[(4-methoxypyrimidin-5-yl)methyl]pyridine-3-carboxamide | | free base/ acid | |
| 83 | 5-chloro-6-cyclopropyl-N-[(4-methoxypyrimidin-5-yl)methyl]pyridine-3-carboxamide | | free base/ acid | |
| 84 | 3-chloro-5-fluoro-4-methoxy-N-[(4-methoxypyrimidin-5-yl)methyl]benzamide | | free base/ acid | |
| 85 | 5-chloro-6-ethoxy-N-[(4-methoxypyrimidin-5-yl)methyl]pyridine-3-carboxamide | | free base/ acid | |
| 86 | N-[(4-ethoxypyrimidin-5-yl)methyl]-3,5-difluoro-4-methoxybenzamide | | free base/ acid | |

TABLE 1-11-continued

| Ex. No. | IUPAC name | structural formula | salt | MS |
|---|---|---|---|---|
| 87 | 4-(difluoromethoxy)-N-[(4-ethoxypyrimidin-5-yl)methyl]-3,5-difluorobenzamide | | free base/ acid | |
| 88 | 5-chloro-6-(difluoromethoxy)-N-[(4-ethoxypyrimidin-5-yl)methyl]pyridine-3-carboxamide | | free base/ acid | |

TABLE 1-12

| Ex. No. | IUPAC name | structural formula | salt | MS |
|---|---|---|---|---|
| 89 | 3,5-difluoro-4-methoxy-N-[(4-methoxypyridin-3-yl)methyl]benzamide | | free base/ acid | |
| 90 | 3,5-difluoro-N-[(5-fluoro-4-methoxypyridin-3-yl)methyl]-4-methoxybenzamide | | free base/ acid | |
| 91 | N-{[4-(cyclopropyloxy)pyrimidin-5-yl]methyl}-6-(1,1-difluoroethyl)-5-fluoropyridine-3-carboxamide | | free base/ acid | |
| 92 | 6-(1,1-difluoroethyl)-5-fluoro-N-[(4-methoxypyrimidin-5-yl)methyl]pyridine-3-carboxamide | | free base/ acid | |

TABLE 1-12-continued

| Ex. No. | IUPAC name | structural formula | salt | MS |
|---|---|---|---|---|
| 93 | 6-(1,1-difluoroethyl)-5-fluoro-N-[(4-methylpyridin-3-yl)methyl]pyridine-3-carboxamide | | free base/ acid | |
| 94 | 6-(1,1-difluoroethyl)-5-fluoro-N-[(5-fluoro-4-methylpyridin-3-yl)methyl]pyridine-3-carboxamide | | free base/ acid | |
| 95 | 5-chloro-N-{[4-(cyclopropyloxy)pyrimidin-5-yl]methyl}-6-(1,1-difluoroethyl)pyridine-3-carboxamide | | free base/ acid | |
| 96 | 5-chloro-6-(1,1-difluoroethyl)-N-[(4-methoxypyrimidin-5-yl)methyl]pyridine-3-carboxamide | | free base/ acid | |

TABLE 1-13

| Ex. No. | IUPAC name | structural formula | salt | MS |
|---|---|---|---|---|
| 97 | 5-chloro-6-(1,1-difluoroethyl)-N-[(4-methylpyridin-3-yl)methyl]pyridine-3-carboxamide | | free base/ acid | |
| 98 | 5-chloro-6-(1,1-difluoroethyl)-N-[(5-fluoro-4-methylpyridin-3-yl)methyl]pyridine-3-carboxamide | | free base/ acid | |

TABLE 1-13-continued

| Ex. No. | IUPAC name | structural formula | salt | MS |
|---|---|---|---|---|
| 99 | 6-(difluoromethoxy)-N-{[4-(difluoromethoxy)pyridin-3-yl]methyl}-5-fluoropyridine-3-carboxamide | | free base/ acid | |
| 100 | 5-(difluoromethyl)-N-[(4-methylpyridin-3-yl)methyl]thiophene-3-carboxamide | | free base/ acid | |
| 101 | 6-(2,2-difluorocyclopropyl)-5-fluoro-N-[(4-methylpyridin-3-yl)methyl]pyridine-3-carboxamide | | free base/ acid | |
| 102 | 5-chloro-6-(2,2-difluorocyclopropyl)-N-[(4-methylpyridin-3-yl)methyl]pyridine-3-carboxamide | | free base/ acid | |
| 103 | 6-(2,2-difluorocyclopropyl)-5-fluoro-N-[(5-fluoro-4-methylpyridin-3-yl)methyl]pyridine-3-carboxamide | | free base/ acid | |
| 104 | 5-chloro-6-(2,2-difluorocyclopropyl)-N-[(5-fluoro-4-methylpyridin-3-yl)methyl]pyridine-3-carboxamide | | free base/ acid | |

TABLE 1-14

| Ex. No. | IUPAC name | structural formula | salt | MS |
|---|---|---|---|---|
| 105 | 6-(difluoromethoxy)-N-[(2,3-dihydrofuro[3,2-c]pyridin-7-yl)methyl]-5-fluoropyridine-3-carboxamide | | free base/ acid | |

TABLE 1-14-continued

| Ex. No. | IUPAC name | structural formula | salt | MS |
|---|---|---|---|---|
| 106 | N-[(2,3-dihydrofuro[3,2-c]pyridin-7-yl)methyl]-3,5-difluoro-4-methoxybenzamide | | free base/ acid | |
| 107 | 6-(difluoromethoxyl)-N-[(2,3-dihydrofuro[2,3-c]pyridin-4-yl)methyl]-5-fluoropyridine-3-carboxamide | | free base/ acid | |
| 108 | N-[(2,3-dihydrofuro[2,3-c]pyridin-4-yl)methyl]-3,5-difluoro-4-methoxybenzamide | | free base/ acid | |
| 109 | 5-fluoro-6-(1-fluorocyclopropyl)-N-[(4-methylpyridin-3-yl)methyl]pyridine-3-carboxamide | | free base/ acid | |
| 110 | 6-(difluoromethoxy)-5-fluoro-N-[(6-methoxypyridazin-4-yl)methyl]pyridine-3-carboxamide | | free base/ acid | |
| 111 | 5-chloro-6-(difluoromethoxy)-N-[(4-(difluoromethoxy)pyridin-3-yl)methyl]pyridine-3-carboxamide | | free base/ acid | |
| 112 | N-[(4-(difluoromethoxy)-pyridin-3-yl)methyl]-3-fluoro-4-(trifluoromethoxy)-benzamide | | free base/ acid | |

TABLE 1-14-continued

| Ex. No. | IUPAC name | structural formula | salt | MS |
|---|---|---|---|---|
| 113 | 6-(1,1-difluoroethyl)-N-[(2,3-dihydrofuro[2,3-c]pyridin-4-yl)methyl]-5-fluoropyridine-3-carboxamide | | free base/ acid | |
| 114 | 5-chloro-6-(1,1-difluoroethyl)-N-[(2,3-dihydrofuro[2,3-c]pyridin-4-yl)methyl]pyridine-3-carboxamide | | free base/ acid | |

TABLE 1-15

| Ex. No. | IUPAC name | structural formula | salt | MS |
|---|---|---|---|---|
| 115 | 5-chloro-6-(2,2-difluorocyclopropyl)-N-[(5-fluoro-4-methylpyridin-3-yl)methyl]pyridine-3-carboxamide<br>Chiral Column Retention time: short | | | 356.0 |
| 116 | 5-chloro-6-(2,2-difluorocyclopropyl)-N-[(5-fluoro-4-methylpyridin-3-yl)methyl]pyridine-3-carboxamide<br>Chiral Column Retention time: long | | | 356.0 |
| 117 | 5-chloro-6-(2,2-difluorocyclopropyl)-N-[(4-methylpyridin-3-yl)methyl]pyridine-3-carboxamide<br>Chiral Column Retention time: short | | | 337.9 |

TABLE 1-15-continued

| Ex. No. | IUPAC name | structural formula | salt | MS |
|---|---|---|---|---|
| 118 | 5-chloro-6-(2,2-difluorocyclopropyl)-N-[(4-methylpyridin-3-yl)methyl]pyridine-3-carboxamide<br>Chiral Column Retention time: long | | | 337.9 |
| 119 | N-[(2,3-dihydrofuro[2,3-c]pyridin-4-yl)methyl]-5-fluoro-6-methoxypyridine-3-carboxamide | | | 304.0 |
| 120 | N-[(2,3-dihydrofuro[2,3-c]pyridin-4-yl)methyl]-3-fluoro-4-methoxybenzamide | | | 303.0 |
| 121 | 5-chloro-N-[(2,3-dihydrofuro[2,3-c]pyridin-4-yl)methyl]-6-(trifluoromethyl)pyridine-3-carboxamide | | | 358.0 |
| 122 | 4-(difluoromethyl)-N-[(2,3-dihydrofuro[2,3-c]pyridin-4-yl)methyl]-3-fluorobenzamide | | | 323.0 |

TABLE 1-16

| Ex. No. | IUPAC name | structural formula | salt | MS |
|---|---|---|---|---|
| 123 | 6-(2,2-difluorocyclopropyl)-N-[(2,3-dihydrofuro[2,3-c]pyridin-4-yl)methyl]-5-fluoropyridine-3-carboxamide<br>Chiral Column Retention time: short | | | 350.2 |
| 124 | 6-(2,2-difluorocyclopropyl)-N-[(2,3-dihydrofuro[2,3-c]pyridin-4-yl)methyl]-5-fluoropyridine-3-carboxamide<br>Chiral Column Retention time: long | | | 350.1 |

Experimental Example 1 NR2B Ca²⁺ Influx Assay

To confirm the "antagonistic action on an NMDA receptor containing the NR2B subunit" of the compound of the present invention, human embryonic kidney cell expressing the "NMDA receptor composed of four subunits including 2 sets of heterodimers of NR1 and NR2B", specifically HEK293 cell expressing human glutamate ionotropic receptor NMDA type subunit 1 (GRIN1) and human glutamate ionotropic receptor NMDA type subunit 2B (GRIN2B), was used and the activation suppressive effect (inhibitory activity) on the receptors by the compound of the present invention was measured.

HEK293 cells that express GRIN1 and GRIN2B were purchased from ChanTest (Human NMDA (NR1/NR2B) Receptor-expressing, stable replicating cell line (HEK293) catalog No. CT6121).

As an index of the NMDA receptor activation, intracellular calcium ion ($Ca^{2+}$) influx caused by the binding of glycine and glutamic acid with NR1 and NR2B, respectively, was used.

HEK293 cells that express GRIN1 and GRIN2B were cultured in a cell culture flask in DMEM/F-12 (COSMO BIO, 10-092-CM) medium added with 10% FBS (fetal bovine serum, AusGene), 100 units/mL penicillin, 100 μg/mL streptomycin, 500 μg/mL neomycin, 100 μg/mL Zeocin (registered trade mark, Invitrogen), 5 μg/mL Blasticidin, in an incubator (37° C., 5% $CO_2$).

The cells were detached from flask with trypsin the day before the assay, suspended in a seeding medium (DMEM (Invitrogen, 31053) added with 10% FBS, 100 units/mL penicillin, 100 μg/mL streptomycin) at $8\times10^5$ cells/mL, seeded by 25 μL/well in a 384-well plate (Falcon, 356663) at 20000 cells/well, and cultured overnight in an incubator. On the day of the assay, tetracycline (Wako Pure Chemical Industries, Ltd., 209-16561) was diluted with the seeding medium at 2 μg/mL, added at 25 μL/well to the plate seeded with the cells, and cultured for 2 hr in an incubator. Thereafter, the medium was removed, and the cells were washed with 50 μL/well assay buffer (137 mM NaCl, 4 mM KCl, 1.8 mM $CaCl_2$, 10 mM HEPES (pH 7.2), 10 mM Glucose, 0.1% BSA). Then, a loading buffer (assay buffer added with 2.5 μM Fluo-4AM, 2 mM Amaranth, 1 mM Tartrazine) was added at 25 μL/well, and incubation was performed in the incubator for 30 min, and at room temperature for 15 min. A solution (25 μL/well) of the Example compound diluted with the above-mentioned assay buffer at 30 μM (final concentration 10 μM) was added, and the cells were stood for 15 min at room temperature. Using FDSS7000EX/μCELL (Hamamatsu Photonics K.K.), 25 μL/well of an assay buffer containing 30 μM glutamic acid, 30 μM glycine was added, and the fluorescence signal at wavelength of Excitation 480 nm, Emission 540 nm was measured every 3 seconds for 5 min. The inhibitory activity was calculated as a relative activity value (inhibitory rate) that inhibits 100% of the cumulative value of the fluorescence value of a well added with an assay buffer free of glutamic acid, glycine, relative to the cumulative value of the fluorescence value of each well. The results are shown in Table 2.

TABLE 2-1

| Example No. | inhibitory rate (10 μM compound concentration) |
|---|---|
| 1 | 95% |
| 2 | 93% |
| 3 | 95% |
| 4 | 96% |
| 5 | 94% |
| 6 | 95% |
| 7 | 91% |
| 8 | 95% |
| 9 | 90% |
| 10 | 96% |
| 11 | 95% |
| 12 | 92% |
| 13 | 93% |
| 14 | 96% |
| 15 | 96% |
| 16 | 94% |
| 17 | 98% |
| 18 | 96% |
| 19 | 91% |
| 20 | 94% |
| 21 | 93% |
| 22 | 95% |
| 23 | 95% |
| 24 | 95% |
| 25 | 88% |
| 26 | 93% |
| 27 | 95% |
| 28 | 87% |
| 29 | 92% |
| 30 | 92% |
| 31 | 68% |
| 32 | 96% |
| 33 | 94% |
| 34 | 97% |
| 35 | 96% |
| 36 | 92% |
| 37 | 84% |

TABLE 2-2

| Example No. | inhibitory rate (10 μM compound concentration) |
|---|---|
| 38 | 94% |
| 39 | 97% |
| 40 | 96% |
| 41 | 94% |
| 42 | 94% |
| 43 | 90% |
| 44 | 79% |
| 45 | 91% |
| 46 | 95% |
| 47 | 97% |
| 48 | 88% |
| 49 | 94% |
| 50 | 90% |
| 51 | 87% |
| 52 | 83% |
| 53 | 91% |
| 54 | 94% |
| 55 | 91% |
| 56 | 93% |
| 57 | 78% |
| 58 | 85% |
| 59 | 93% |
| 60 | 88% |
| 61 | 95% |
| 62 | 87% |
| 63 | 90% |
| 64 | 85% |
| 65 | 93% |
| 66 | 84% |
| 67 | 92% |
| 68 | 93% |
| 69 | 94% |
| 70 | 91% |
| 71 | 91% |
| 72 | 87% |

TABLE 2-2-continued

| Example No. | inhibitory rate (10 μM compound concentration) |
|---|---|
| 73 | 93% |
| 74 | 90% |

TABLE 2-3

| Example No. | inhibitory rate (10 μM compound concentration) |
|---|---|
| 75 | 93% |
| 76 | 95% |
| 77 | 94% |
| 78 | 94% |
| 79 | 89% |
| 80 | 94% |
| 81 | 90% |
| 82 | 89% |
| 83 | 92% |
| 84 | 91% |
| 85 | 87% |
| 86 | 90% |
| 87 | 93% |
| 88 | 92% |
| 89 | 92% |
| 90 | 95% |
| 91 | 91% |
| 92 | 86% |
| 93 | 90% |
| 94 | 91% |
| 95 | 90% |
| 96 | 85% |
| 97 | 92% |
| 98 | 95% |
| 99 | 89% |
| 100 | 72% |
| 101 | 90% |
| 102 | 93% |
| 103 | 92% |
| 104 | 95% |
| 111 | 94% |
| 112 | 96% |

As shown in the above-mentioned Table 2, the compound of the present invention suppressed intracellular calcium ion ($Ca^{2+}$) influx in the NMDA receptors containing the NR2B subunit. That is, it has been confirmed that the compound of the present invention has an antagonistic action on an NMDA receptor containing the NR2B subunit.

Experimental Example 2 [$^3$H]MK-801 Binding Test In Vivo

In order to confirm "functional antagonistic action on an NMDA receptor containing the NR2B subunit in vivo" which the compound of the present invention has, binding test was performed using tritium-labeled form of MK-801 ((5R,10S)-5-methyl-10,11-dihydro-5H-5,10-epiminod-ibenzo[a,d][7]annulene) ([$^3$H]MK-801), which is a compound capable of binding to the opening site of the NMDA receptor.

The example compound (1 mg/kg/2 mL, 0.5% MC water) or vehicle (kg/2 mL, 0.5% MC water) was orally administered (p.o.) to Sprague Dawley rats (body weight 180-260 g). After a certain time (around after time-to maximum blood concentration), [$^3$H]MK-801 (20 μCi/kg/mL, Muromachi Kikai) was intravenously administered. After 10 min, the rats were euthanized by decapitation, and subjected to craniotomy, and the hippocampus was collected. The collected hippocampus was homogenized in 30 volumes (30 mL per 1 g tissue) ice-cooled 20 mM Hepes (pH7.5, Hampton Research) using a homogenizer (T10 basic Ultra-Turrax) for sec. Then, 600 μL of the homogenate was immediately filtered through GF/B Whatman glass filter (GE Health Cane), which were presoaked in 0.5% polyethyleneimine (FUJIFILM Wako Pure Chemical Corporation) and set on Manifold Filtration System (Millipore) by suction. The filter was washed four times with ice-cooled saline (5 mL, Otsuka Pharmaceutical), put into a scintillation vial, and then 10 mL of liquid scintillator A (FUJIFILM Wako Pure Chemical Corporation) was added thereto, and the residual radioactivity was counted using liquid scintillation counter (ALOKA LSC-6100). Separately, the residual radioactivity in 100 μL of the homogenate before the filtration was counted in the same way. The value of [the residual radioactivity in the filter/the residual radioactivity in the 100 μL of the homogenate] was calculated as a [$^3$H]MK-801 binding rate to the NMDA receptor expressing in each individual hippocampus tissue. Then, the [$^3$H]MK-801 binding rate in the vehicle control group was regarded as 100%, and the [$^3$H]MK-801 binding rate in the group subcutaneously administered with excess amount of MK-801 maleate (2 mg/kg/2 mL, 0.5% MC water) was regarded as 0%. The difference between the percentage of [$^3$H]MK-801 binding rate in the group orally administered with the example compound and that in the vehicle control group (100%) was analyzed as [$^3$H]MK-801 binding inhibitory rate by the example compound. The results are shown in Table 3.

TABLE 3

| Example No. | inhibitory rate (1 mg/kg, p.o.) |
|---|---|
| 12 | 23% |
| 42 | 14% |
| 63 | 10% |

As shown in the above-mentioned Table 3, the compound of the present invention inhibited the binding of [$^3$H]MK-801 which is a compound capable of binding to the opening site of the NMDA receptor containing the NR2B subunit. That is, the compound of the present invention was confirmed to have a functional antagonistic action on an NMDA receptor containing the NR2B subunit in vivo.

Formulation Example 1 (Production of Capsule)

| 1) compound of Example 1 | 30 mg |
|---|---|
| 2) finely-powdered cellulose | 10 mg |
| 3) lactose | 19 mg |
| 4) magnesium stearate | 1 mg |
| | total 60 mg |

1), 2), 3) and 4) are mixed and filled in a gelatin capsule

Formulation Example 2 (Production of Tablets)

| 1) compound of Example 1 | 30 g |
|---|---|
| 2) lactose | 50 g |
| 3) cornstarch | 15 g |

-continued

| | |
|---|---|
| 4) calcium carboxymethylcellulose | 44 g |
| 5) magnesium stearate | 1 g |
| 1000 tablets | total 140 g |

The total amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Example 1 per tablet are obtained.

INDUSTRIAL APPLICABILITY

The compound of the present invention can have an antagonistic action on an NMDA receptor containing the NR2B subunit, and is expected to be useful as a prophylactic or therapeutic agent for depression, bipolar disorder, migraine, pain, peripheral symptoms of dementia and the like.

The invention claimed is:
1. A compound represented by the formula (I):

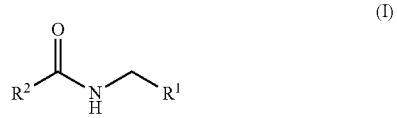

wherein
R$^1$ is

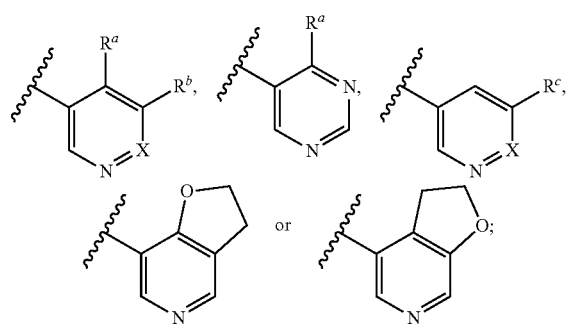

wherein
X is CH or a nitrogen atom;
R$^a$ is
(1) a C$_{1-3}$ alkyl group optionally substituted by fluorine atom(s),
(2) a C$_{3-6}$ cycloalkyl group optionally substituted by fluorine atom(s),
(3) a C$_{1-6}$ alkoxy group optionally substituted by fluorine atom(s), or
(4) a C$_{3-6}$ cycloalkyloxy group optionally substituted by fluorine atom(s);
R$^b$ is
(1) a hydrogen atom,
(2) a C$_{1-6}$ alkyl group optionally substituted by fluorine atom(s),
(3) a C$_{1-6}$ alkoxy group optionally substituted by fluorine atom(s), or
(4) a halogen atom; and R$^c$ is
(1) a C$_{2-6}$ alkyl group optionally substituted by fluorine atom(s),
(2) a C$_{1-6}$ alkoxy group optionally substituted by fluorine atom(s), or
(3) a halogen atom; and
R$^2$ is
(1)

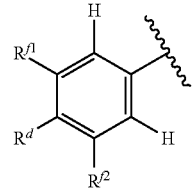

wherein
R$^d$ is
(a) a C$_{3-6}$ cycloalkyl group optionally substituted by fluorine atom(s),
(b) a C$_{1-6}$ alkoxy group optionally substituted by fluorine atom(s),
(c) a C$_{3-6}$ cycloalkyloxy group optionally substituted by fluorine atom(s),
(d) a difluoromethyl group, or
(e) a trifluoromethyl group; and
R$^{f1}$ and R$^{f2}$ are each independently a hydrogen atom, a fluorine atom, a chlorine atom, or a methyl group,
(2)

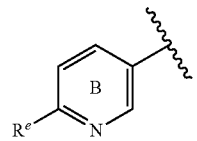

wherein
R$^e$ is
(a) a C$_{3-6}$ cycloalkyl group optionally substituted by fluorine atom(s),
(b) a C$_{1-6}$ alkoxy group optionally substituted by fluorine atom(s),
(c) a C$_{3-6}$ cycloalkyloxy group optionally substituted by fluorine atom(s), or
(d) a C$_{1-2}$ alkyl group substituted by fluorine atom(s); and
ring B is optionally further substituted by 1 to 3 substituents selected from a fluorine atom, a chlorine atom, and a methyl group, or
(3)

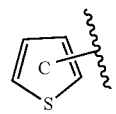

wherein
ring C is further substituted by 1 or 2 substituents selected from
(a) a C$_{3-6}$ cycloalkyl group optionally substituted by fluorine atom(s),
(b) a C$_{1-6}$ alkoxy group optionally substituted by fluorine atom(s), (c) a $C_{3-6}$ cycloalkyloxy group optionally substituted by fluorine atom(s), and
(d) a $C_{1-2}$ alkyl group substituted by fluorine atom(s), or a pharmacologically acceptable salt thereof.

2. The compound according to claim 1, wherein $R^1$ is

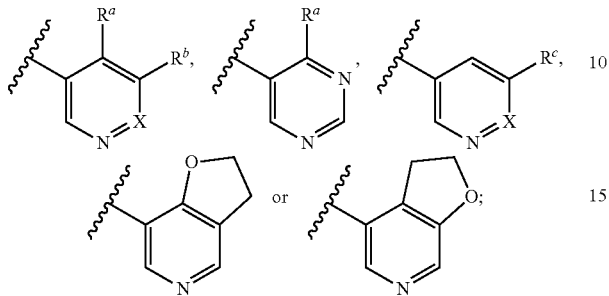

or wherein
X is CH or a nitrogen atom;
$R^a$ is
(1) a $C_{1-3}$ alkyl group optionally substituted by 1 to 3 fluorine atoms,
(2) a $C_{3-6}$ cycloalkyl group optionally substituted by 1 to 3 fluorine atoms,
(3) a $C_{1-6}$ alkoxy group optionally substituted by 1 to 3 fluorine atoms, or
(4) a $C_{3-6}$ cycloalkyloxy group optionally substituted by 1 to 3 fluorine atoms;
$R^b$ is
(1) a hydrogen atom, or
(2) a halogen atom; and
$R^c$ is
(1) a $C_{1-6}$ alkoxy group optionally substituted by 1 to 3 fluorine atoms, or
(2) a halogen atom; and
$R^2$ is
(1)

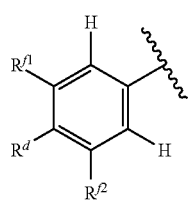

wherein
$R^d$ is
(a) a $C_{1-6}$ alkoxy group optionally substituted by 1 to 3 fluorine atoms,
(b) a difluoromethyl group, or
(c) a trifluoromethyl group; and
$R^{f1}$ and $R^{f2}$ are each independently a hydrogen atom, fluorine atom, or chlorine atom,
(2)

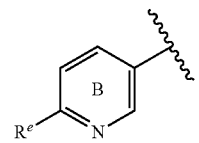

wherein
$R^e$ is
(a) a $C_{3-6}$ cycloalkyl group optionally substituted by 1 to 3 fluorine atoms,
(b) a $C_{1-6}$ alkoxy group optionally substituted by 1 to 3 fluorine atoms, or
(c) a $C_{1-2}$ alkyl group substituted by 1-5 fluorine atoms; and
ring B is optionally further substituted by 1 to 3 substituents selected from a fluorine atom, and a chlorine atom, or
(3)

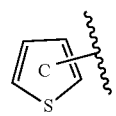

wherein
ring C is further substituted by 1 or 2 substituents selected from
(a) a $C_{3-6}$ cycloalkyl group optionally substituted by 1 to 3 fluorine atoms, and
(b) a $C_{1-2}$ alkyl group substituted by 1 to 3 fluorine atoms, or a pharmacologically acceptable salt thereof.

3. A medicament comprising the compound according to claim 1 or a pharmacologically acceptable salt thereof and a pharmacologically acceptable carrier.

4. A method for treating depression, bipolar disorder, migraine, pain, or peripheral symptoms of dementia in a mammal, comprising administering an effective amount of the compound according to claim 1 or a pharmacologically acceptable salt thereof to the mammal.

5. A method according to claim 4, wherein the mammal is a human.

* * * * *